US011573239B2

(12) United States Patent
Shan et al.

(10) Patent No.: US 11,573,239 B2
(45) Date of Patent: Feb. 7, 2023

(54) METHODS AND SYSTEMS FOR DE NOVO PEPTIDE SEQUENCING USING DEEP LEARNING

(71) Applicant: BIOINFORMATICS SOLUTIONS INC., Waterloo (CA)

(72) Inventors: Baozhen Shan, Waterloo (CA); Ngoc Hieu Tran, Waterloo (CA); Ming Li, Waterloo (CA); Lei Xin, Waterloo (CA); Xianglilan Zhang, Waterloo (CA)

(73) Assignee: BIOINFORMATICS SOLUTIONS INC., Waterloo (CA)

( * ) Notice: Subject to any disclaimer, the term of this patent is extended or adjusted under 35 U.S.C. 154(b) by 1165 days.

(21) Appl. No.: 16/037,949

(22) Filed: Jul. 17, 2018

(65) Prior Publication Data
US 2019/0018019 A1    Jan. 17, 2019

Related U.S. Application Data

(60) Provisional application No. 62/533,560, filed on Jul. 17, 2017.

(51) Int. Cl.
*G01N 33/48* (2006.01)
*G01N 33/50* (2006.01)
(Continued)

(52) U.S. Cl.
CPC ..... *G01N 33/6851* (2013.01); *G01N 33/6818* (2013.01); *G01N 33/6848* (2013.01);
(Continued)

(58) Field of Classification Search
CPC ........... G01N 33/6851; G01N 33/6818; G01N 33/6848; G06F 17/16; G16B 20/00; G16B 30/20; G16B 40/00; G16B 40/10; G16B 40/20; G16B 50/00; G16B 50/10; G16B 50/20
See application file for complete search history.

(56) References Cited

U.S. PATENT DOCUMENTS

2017/0200066 A1* 7/2017 Wang .................. G06K 9/6269

FOREIGN PATENT DOCUMENTS

WO    2005/057208 A1    6/2005

OTHER PUBLICATIONS

Tran et al. De novo peptide sequencing by deep learning. PNAS, vol. 114, Aug. 1, 2017, pp. 8247-8252.*

(Continued)

*Primary Examiner* — Russell S Negin
(74) *Attorney, Agent, or Firm* — Norton Rose Fulbright Canada LLP

(57) ABSTRACT

The present systems and methods introduce deep learning to de novo peptide sequencing from tandem mass spectrometry data. The systems and methods achieve improvements in sequencing accuracy over existing systems and methods and enables complete assembly of novel protein sequences without assisting databases. The present systems and methods are re-trainable to adapt to new sources of data and provides a complete end-to-end training and prediction solution, which is advantageous given the growing massive amount of data. The systems and methods combine deep learning and dynamic programming to solve optimization problems.

32 Claims, 25 Drawing Sheets
Specification includes a Sequence Listing.

(51) Int. Cl.
| | |
|---|---|
| G01N 33/68 | (2006.01) |
| G06F 17/16 | (2006.01) |
| G16B 20/00 | (2019.01) |
| G16B 40/00 | (2019.01) |
| G16B 50/00 | (2019.01) |
| G16B 30/20 | (2019.01) |
| G16B 40/10 | (2019.01) |
| G16B 40/20 | (2019.01) |
| G16B 50/20 | (2019.01) |
| G16B 50/10 | (2019.01) |

(52) U.S. Cl.
CPC .......... G06F 17/16 (2013.01); G16B 20/00 (2019.02); G16B 30/20 (2019.02); G16B 40/00 (2019.02); G16B 40/10 (2019.02); G16B 40/20 (2019.02); G16B 50/00 (2019.02); G16B 50/10 (2019.02); G16B 50/20 (2019.02)

(56) References Cited

OTHER PUBLICATIONS

Tanner et al. InsPecT: Identification of posttranslationally modified peptides from tandem mass spectra. Analytical Chemistry, vol. 77, pp. 4626-4639. (Year: 2005).*
International Search Report and Written Opinion issued in International Application No. PCT/CA2018/051628, dated Apr. 10, 2019.
Seidler et al., "De Novo Sequencing of Peptides by MS/MS", Proteomics Journal, vol. 10, Issue 4, Feb. 18, 2010, pp. 634 to 639.
Catusse, J., Strub, J.-M., Job, C., Van Dorsselaer, A. & Job, D. Proteome-wide characterization of sugarbeet seed vigor and its tissue specific expression Proc. Natl. Acad Sci. U.S.A. 105, 10262-10267 (2008).
Novo, J.V.J., Pascual, J., Lucas, R.S., Romero-Rodriguez, C., Ortega, M.R., Lenz, C. & Valledor, L. Fourteen years of plant proteomics reflected in Proteomics: moving from model species and 2DE-based approaches to orphan species and gel-free platforms. Proteomics 15, 1089-1112 (2015).
Maggon, K. Monoclonal antibody "gold rush". Curr. Med. Chem. 14, 1978-1987 (2007).
Tran., N.H., Rahman, M.Z., He, L., Xin, L., Shan, B.Z. & Li, M. Complete de novo assembly of monoclonal antibody sequences. Scientific Reports 6, 31730 (2016).
LeCun, Y., Bengio, Y. & Hinton, G. Deep learning. Nature 521, 436-444 (2015).
Ciresan, D., Giusti, A., Gambardella, L.M. & Schmidhuber, J. Deep neural networks segment neuronal membranes in electron microscopy images. In Proc Advances in Neural Information Processing Systems 25, (2012).
Krizhevsky, A., Sutskever, I. & Hinton, G. ImageNet classification with deep convolutional neural networks. In Proc. Advances in Neural Information Processing Systems 25, (2012).
Hinton, G. et al. Deep neural networks for acoustic modeling in speech recognition: the shared views of four research groups. IEEE Signal Processing Magazine 29, 82-97 (2012).
Sutskever, I., Vinyals, O. & Le, Q. Sequence to sequence learning with neural networks. In Proc. Advances in Neural Information Processing Systems 27, 3104 3112 (2014).
Glorot, X., Bordes, A. & Bengio, Y. Deep sparse rectifier neural networks. Proceedings of the Fourteenth International Conference on Artificial Intelligence and Statistics (AISTATS), (2011).
Zhou, J. & Troyanskaya, O.G. Predicting effects of noncoding variants with deep learning based sequence model. Nat. Methods 12, 931-934 (2015).
Alipanahi, B., Delong, A., Weirauch, M.T. & Frey, B.J. Predicting the sequence specificities of DNA- and RNA-binding proteins by deep learning. Nat. Biotechnology 33, 831-838 (2015).
Wang, S., Sun, S., Li, Z., Zhang, R. & Xu, JB. Accurate de novo prediction of protein contact map by ultra-deep learning model PLoS Comput. Biol. 13, e1005324 (2017).
Hochreiter, S. & Schmidhuber, J. Long short-term memory. Neural Computation 9, 1735-1780 (1997).
Karpathy, A. & Li, F.F. Deep visual-semantic alignments for generating image description. IEEE Conference on Computer Vision and Pattern Recognition (CVPR), 3128-3137 (2015).
Vinyals, O., Toshev, A., Bengio, S. & Erhan, D. Show and tell: a neural image caption generator. IEEE Conference on Computer Vision and Pattern Recognition (CVPR), 3156-3164 (2015).
Mikolov, T., Sutskever, I., Chen, K., Corrado, G. & Dean, J. Distributed representations of words and phrases and their compositionality. In Proc. Advances in Neural Information Processing Systems 26, 3111-3119 (2013).
Lecun, Y. et al. Backpropagation applied to handwritten zip code recognition. Neural Comput. 11, 541-551 (1989).
Grosche A. et al. The proteome of native adult Muller Glial cells from murine retina. Mol. Cell. Proteomics 15, 462-480 (2016).
Marza, E. et al. Genome-wide screen identifies a novel p97/CDC-48-dependent pathway regulating ER-stress-induced gene transcription. EMBO Rep. 16, 332-340 (2015).
Pettersen, V.K., Mosevoll, K.A., Lindemann, P.C. & Wiker, H.G. Coordination of metabolism and virulence factors expression of extraintestinal pathogenic *Escherichia coli* purified from blood cultures of patients with sepsis. Mol. Cell. Proteomics 15, 2890-2907 (2016).
Hu, H. et al. Proteome analysis of the hemolymph, mushroom body, and antenna provides novel insight into honeybee resistance against varroa infestation. J. Proteome Res., 15, 841-854 (2016).
Hebert A.S. et al. The one hour yeast proteome. Mol Cell. Proteomics. 13, 339-347 (2014).
Cypryk, W. et al. Proteomic and bioinformatic characterization of extracellular vesicles released from human macrophages upon Influenza A virus infection J. Proteome Res., 16, 217-227 (2017).
Inglese, P. et al. Deep learning and 3D-DESI imaging reveal the hidden metabolic heterogeneity of cancer. Chem. Sci. (2017).
Davis, J. & Goadrich, M. The relationship between Precision-Recall and ROC curves. Proceedings of the 23rd International Conference on Machine Learning, 233-240 (2006).
Kingma, D.P. & Ba, J. Adam: a method for stochastic optimization. arXiv:1412.6980.
Kall, L., Cantebury, J.D., Weston, J., Noble, W.S. & MacCoss, M.J. Semi-supervised learning for peptide identification from shotgun proteomics datasets. Nat. Methods 4, 923-925 (2007).
Paiva, A.L., Oliveira, J.T., de Souza, G.A. & Vasconcelos, I.M. Label-free proteomics reveals that Cowpea severe mosaic virus transiently suppresses the host leaf protein accumulation during the compatible interaction with Cowpea (*Vigna unguiculata* [L.] Walp.). J. Proteome Res., 15, 4208-4220 (2016).
Nevo, N. et al. Impact of cystinosin glycosylation on protein stability by differential dynamic stable isotope labeling by amino acids in cell culture (SILAC). Mol Cell Proteomics, 16, 457-468 (2017).
Cassidy, L., Prasse, D., Linke, D., Schmitz, R.A. & Tholey, A. Combination of bottom-up 2DLC-MS and semi-top-down GelFree-LC-MS enhances coverage of proteome and low molecular weight short open reading frame encoded peptides of the Archaeon Methanosarcina mazei. J. Proteome Res., 15, 3773-3783 (2016).
Reuß, D.R. et al. Large-scale reduction of the Bacillus subtilis genome: consequences for the transcriptional network, resource allocation, and metabolism. Genome Res., 27, 289-299 (2017).
Petersen, J.M. et al. Chemosynthetic symbionts of marine invertebrate animals are capable of nitrogen fixation. Nat. Microbiol., 2, 16195 (2016).
Seidel, G. et al. Quantitative global proteomics of Yeast PBP1 deletion mutants and their stress responses identifies glucose metabolism, mitochondrial, and stress granule changes. J. Proteome Res., 16, 504 515 (2017).
Johnson, R.S. & Biemann, K. The primary structure of thioredoxin from Chromatium vinosum determined by high-performance tandem mass spectrometry. Biochemistry 26, 1209-1214 (1987).

(56) References Cited

OTHER PUBLICATIONS

Martin-Visscher, L.A., van Belkum, M.J., Gameau-Tsodikova, S., Whiltal, R.M., Zheng, J., McMullen, L.M., & Vederas, J.C. Isolation and characterization of carnocyclin a, a novel circular bacteriocin produced by Carnobacterium maltaromaticum UAL307. Appl. Environ. Microbiol. 74, 4756-4763 (2008).

Hatano, N. & Hamada, T. Proteome analysis of pitcher fluid of the carnivorous plant Nepenthes alata. J. Proteome Res. 7, 809-816 (2008).

Mata, C.I. et al. In-depth characterization of the tomato fruit pericarp proteome. Proteomics, 17, 1-2 (2017).

Srivastava, N., Hinton, G., Krizhevsky, A., Sutskever, I. & Salakhutdinov, R. Dropout: a simple way to prevent neural networks from overfitting. J. Mach. Learn. Res. 15, 1929-1958 (2014).

Taylor, J.A. & Johnson, R.S. Sequence database searches via de novo peptide sequencing by tandem mass spectrometry. Rapid Commun. Mass Spectrom. 11, 1067-1075 (1997).

Taylor, J.A. & Johnson, R.S. Implementation and uses of automated de novo peptide sequencing by tandem mass spectrometry. Anal. Chem. 73, 2594-2604 (2001).

Chen, T., Kao, M.Y., Tepel, M., Rush, J. & Church, G.M. A dynamic programming approach to de novo peptide sequencing via tandem mass spectrometry. J. Comput. Biol. 8, 325-337 (2001).

Dancik, D., Addona, T.A., Clauser, K.R., Vath, J.E. & Pevzner, P.A. De novo peptide sequencing via tandem mass spectrometry. J. Comp. Biol. 6, 327-342 (1999).

Ma, B., Zhang, K., Hendrie, C., Liang, C., Li, M., Doherty-Kirby, A. & Lajoie, G. Peaks: powerful software for peptide de novo sequencing by tandem mass spectrometry. Rapid Commun. Mass Spectrom. 17, 2337-2342 (2003).

Zhang, Z. De novo peptide sequencing based on a divide-and-conquer algorithm and peptide tandem spectrum simulation. Anal. Chem. 76, 6374-6383 (2004).

Frank, A. & Pevzner, P.A. PepNovo: de novo peptide sequencing via probabilistic network modeling. Anal. Chem. 77, 964-973 (2005).

Fischer, B., Roth, V., Roos, F., Grossmann, J., Baginsky, S., Widmayer, P., Gruissem, W. & Buhmann, J.M. NovoHMM: a hidden Markov model for de novo peptide sequencing. Anal. Chem. 77, 7265-7273 (2005).

DiMaggio, P.A. & Floudas, C.A.: De novo peptide identification via tandem mass spectrometry and integer linear optimization. Anal. Chem. 79, 1433-1446 (2007).

Mo, L., Dutta, D., Wan, Y. & Chen, T. MSNovo: a dynamic programming algorithm for de novo peptide sequencing via tandem mass spectrometry. Anal. Chem. 79, 4870-4878 (2007).

Chi, H. et al. pNovo: de novo peptide sequencing and identification using HCD spectra. J. Proteome Res. 9, 2713-2724 (2010).

Jeong, K., Kim, S. & Pevzner, P.A. UniNovo: a universal tool for de novo peptide sequencing. Bioinformatics 29, 1953-1962 (2013).

Chi, H. et al. pNovo+: de novo peptide sequencing using complementary HCD and ETD tandem mass spectra. J. Proteome Res. 12, 615-625 (2013).

Ma, B. Novor. real-time peptide de novo sequencing software. J. Amer. Soc. Mass Spectrom. 26, 1885-1894 (2015).

Tsou, C. et al., DIA-Umpire: Comprehensive Computational Framework for Data-independent Acquisition Proteomics, Nature Methods, vol. 12, No. 3, Nature America, Mar. 2015.

Kim, S. & Pevzner, P.A. MS-GF+ makes progress towards a universal database search tool for proteomics. Nat. Commun. 5, 5277 (2014).

Bandeira, N., Pham, V., Pevzner, P., Arnott, D. & Lill, J.R. Automated de novo protein sequencing of monoclonal antibodies. Nat. Biotechnol. 26, 1336-1338 (2008).

Guthals, A., Clauser, K.R., Frank, A.M., & Bandeira, N. Sequencing-grade de novo analysis of MS/MS triplets (CID/HCD/ETD) from overlapping peptides. J. Proteome Res. 12, 2846-2857 (2013).

Ma, B. & Johnson, R. De novo sequencing and homology searching. Mol. Cell Proteomics 11, O111.014902. (2012).

Steen, H. & Mann, M. The abc's (and xyz's) of peptide sequencing. Nat. Rev. Mol. Cell Biol., 699-711 (2004).

Zhang, Y. et al. Tissue-based proteogenomics reveals that human testis endows plentiful missing proteins. J. Proteome. Res. 14, 3583-3594 (2015).

\* cited by examiner

SEQUENCE LISTING

<160> NUMBER OF SEQ ID NOS: 4

<210> SEQ ID NO 1
<211> LENGTH: 219
<212> TYPE: PRT
<213> ORGANISM: Artificial Sequence
<220> FEATURE:
<223> OTHER INFORMATION: synthesized

<400> SEQUENCE: 1

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Tyr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95
```

```
Ser His Val Pro Leu Thr Phe Gly Ala Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

<210> SEQ ID NO 2
<211> LENGTH: 219
<212> TYPE: PRT
<213> ORGANISM: Artificial Sequence
<220> FEATURE:
<223> OTHER INFORMATION: synthesized

<400> SEQUENCE: 2

```
Asp Val Leu Met Thr Gln Thr Pro Leu Ser Leu Pro Val Ser Leu Gly
1               5                   10                  15

Asp Gln Ala Ser Leu Ser Cys Arg Ser Ser Gln Tyr Leu Val His Ser
            20                  25                  30

Asp Gly Asn Thr Tyr Leu Glu Trp Tyr Leu Gln Lys Pro Gly Gln Ser
        35                  40                  45

Pro Lys Leu Leu Leu Tyr Lys Val Ser Asn Arg Phe Ser Gly Val Pro
    50                  55                  60

Asp Arg Phe Ser Gly Ser Gly Ser Gly Thr Asp Phe Thr Leu Lys Leu
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg Ala Asp Ala Ala Pro Thr Val Ser Leu Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Leu Asn Val Lys Trp Lys Leu Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Leu Val Lys Ser Phe Asn Arg Asn Glu Cys
    210                 215
```

<210> SEQ ID NO 3
<211> LENGTH: 430

<212> TYPE: PRT
<213> ORGANISM: Artificial Sequence
<220> FEATURE:
<223> OTHER INFORMATION: synthesized

<400> SEQUENCE: 3

```
Lys Glu Ser Gly Pro Gly Leu Val Ala Pro Ser Gln Ser Leu Ser Ile
1               5                   10                  15

Thr Cys Thr Val Ser Gly Phe Ser Leu Leu Gly Tyr Gly Val Asn Trp
            20                  25                  30

Val Arg Gln Pro Pro Gly Gln Gly Leu Glu Trp Leu Met Gly Ile Trp
        35                  40                  45

Gly Asp Gly Ser Thr Asp Tyr Asn Ser Ala Leu Lys Ser Arg Ile Ser
    50                  55                  60

Ile Thr Lys Asp Asn Ser Lys Ser Gln Val Phe Leu Lys Met Asn Ser
65                  70                  75                  80

Leu Gln Thr Asp Asp Thr Ala Lys Tyr Tyr Cys Thr Arg Ala Pro Tyr
                85                  90                  95

Gln Tyr Phe Ala Tyr Trp Gly Gln Gly Thr Leu Val Thr Val Ser Ala
            100                 105                 110

Ala Lys Thr Thr Pro Pro Ser Val Tyr Pro Leu Ala Pro Gly Ser Ala
        115                 120                 125

Ala Gln Thr Asp Ser Met Val Thr Leu Gly Cys Leu Val Lys Gly Tyr
    130                 135                 140

Phe Pro Glu Pro Val Thr Val Thr Trp Asn Ser Gly Ser Leu Ser Ser
145                 150                 155                 160

Gly Val His Thr Phe Pro Ala Val Leu Gln Ser Asp Leu Tyr Thr Leu
                165                 170                 175

Ser Ser Ser Val Thr Val Pro Ser Ser Thr Trp Pro Ser Glu Thr Val
            180                 185                 190

Thr Cys Asn Val Ala His Pro Ala Ser Ser Thr Lys Val Asp Lys Lys
        195                 200                 205

Ile Val Pro Arg Asp Cys Gly Cys Lys Pro Cys Ile Cys Thr Val Pro
    210                 215                 220

Glu Val Ser Ser Val Phe Ile Phe Pro Pro Lys Pro Lys Asp Val Leu
225                 230                 235                 240

Thr Ile Thr Leu Thr Pro Lys Val Thr Cys Val Val Val Asp Ile Ser
                245                 250                 255

Lys Asp Asp Pro Glu Val Gln Phe Ser Trp Phe Val Asp Asp Val Glu
            260                 265                 270

Val His Thr Ala His Thr Gln Pro Arg Glu Glu Gln Phe Asn Ser Thr
        275                 280                 285

Phe Arg Ser Val Ser Glu Leu Pro Ile Met His Gln Asp Trp Leu Asn
    290                 295                 300

Gly Lys Glu Phe Lys Cys Arg Val Asn Ser Ala Ala Phe Pro Ala Pro
305                 310                 315                 320

Ile Glu Lys Thr Ile Ser Lys Thr Lys Gly Arg Pro Lys Ala Pro Gln
                325                 330                 335

Val Tyr Thr Ile Pro Pro Pro Lys Glu Gln Met Ala Lys Asp Lys Val
            340                 345                 350

Ser Leu Thr Cys Met Ile Thr Asp Ile Thr Val Glu Trp Gln Trp Asn
        355                 360                 365

Gly Gln Pro Ala Glu Asn Tyr Lys Asn Thr Gln Pro Ile Met Asp Thr
    370                 375                 380
```

```
Asp Gly Ser Tyr Phe Val Tyr Ser Lys Leu Asn Val Gln Lys Ser Asn
385                 390                 395                 400

Trp Glu Ala Gly Asn Thr Phe Thr Cys Ser Val Leu His Glu Gly Leu
            405                 410                 415

His Asn His His Thr Glu Lys Ser Leu Ser His Ser Pro Gly
            420                 425                 430

<210> SEQ ID NO 4
<211> LENGTH: 430
<212> TYPE: PRT
<213> ORGANISM: Artificial Sequence
<220> FEATURE:
<223> OTHER INFORMATION: synthesized

<400> SEQUENCE: 4

Lys Glu Ser Gly Pro Gly Leu Val Ala Pro Ser Gln Ser Leu Ser Leu
1               5                   10                  15

Thr Cys Thr Val Ser Gly Phe Ser Leu Leu Gly Tyr Gly Val Asn Trp
            20                  25                  30

Val Arg Gln Pro Pro Gly Gln Gly Leu Glu Trp Leu Gly Met Leu Trp
        35                  40                  45

Gly Asp Gly Ser Thr Asp Tyr Asn Ser Ala Leu Lys Ser Arg Leu Thr
50                  55                  60

Leu Ser Lys Asp Asn Ser Lys Ser Gln Val Phe Leu Lys Met Asn Ser
65                  70                  75                  80

Leu Gln Thr Asp Asp Thr Ala Lys Tyr Tyr Cys Thr Arg Ala Pro Tyr
                85                  90                  95

Gln Tyr Phe Ala Tyr Trp Gly Gln Gly Thr Leu Val Thr Val Ser Ala
            100                 105                 110

Ala Lys Thr Thr Pro Pro Ser Val Tyr Pro Leu Ala Pro Gly Ser Ala
        115                 120                 125

Ala Gln Thr Asn Ser Met Val Thr Leu Gly Cys Leu Val Lys Gly Tyr
130                 135                 140

Phe Pro Glu Pro Val Thr Val Thr Trp Asn Ser Gly Ser Leu Ser Ser
145                 150                 155                 160

Gly Val His Thr Phe Pro Ala Val Leu Gln Ser Asp Leu Tyr Thr Leu
                165                 170                 175

Ser Ser Ser Val Thr Val Pro Ser Ser Thr Trp Pro Ser Glu Thr Val
            180                 185                 190

Thr Cys Asn Val Ala His Pro Ala Ser Ser Thr Lys Val Asp Lys Lys
        195                 200                 205

Leu Val Pro Arg Asp Cys Gly Cys Lys Pro Cys Leu Cys Thr Val Pro
210                 215                 220

Glu Val Ser Ser Val Phe Leu Phe Pro Pro Lys Pro Lys Asp Val Leu
225                 230                 235                 240

Thr Leu Thr Leu Thr Pro Lys Val Thr Cys Val Val Val Asp Leu Ser
                245                 250                 255

Lys Asp Asp Pro Glu Val His Phe Ser Trp Phe Val Asp Asp Val Glu
            260                 265                 270

Val His Thr Ala Gln Thr His Ala Pro Glu Lys Gln Ser Asn Ser Thr
        275                 280                 285

Leu Arg Ser Val Ser Glu Leu Pro Leu Met His Gln Asp Trp Leu Asn
290                 295                 300

Gly Lys Glu Phe Lys Cys Arg Val Asn Ser Ala Ala Phe Pro Ala Pro
305                 310                 315                 320
```

```
Leu Glu Lys Thr Leu Ser Lys Thr Lys Gly Arg Pro Lys Ala Pro Gln
            325             330             335

Val Tyr Thr Leu Pro Pro Pro Lys Glu Gln Met Ala Lys Asp Lys Val
            340             345             350

Ser Leu Thr Cys Met Leu Thr Asp Leu Thr Val Glu Trp Gln Trp Asn
            355             360             365

Gly Gln Pro Ala Glu Asn Tyr Lys Asn Thr Gln Pro Leu Met Asp Thr
        370             375             380

Asp Gly Ser Tyr Phe Val Tyr Ser Lys Leu Asn Val Gln Lys Ser Asn
385             390             395             400

Trp Glu Ala Gly Asn Thr Phe Thr Cys Ser Val Leu His Glu Gly Leu
            405             410             415

His Asn His His Thr Glu Lys Ser Leu Ser His Ser Pro Gly
            420             425             430
```

METHODS AND SYSTEMS FOR DE NOVO PEPTIDE SEQUENCING USING DEEP LEARNING

CROSS-REFERENCE TO RELATED APPLICATIONS

This application claims all benefit of including priority from U.S. Provisional Application No. 62/338,279, titled "METHODS AND SYSTEMS FOR DE NOVO PEPTIDE SEQUENCING USING DEEP LEARNING" filed on Jul. 17, 2017, which is incorporated herein by reference.

FIELD OF THE INVENTION

The invention relates to the field of protein sequencing and, more specifically, de novo peptide sequencing using deep learning.

BACKGROUND OF THE INVENTION

Proteomics research focuses on large-scale studies to characterize the proteome, the entire set of proteins, in a living organism [1-5]. In proteomics, de novo peptide sequencing from tandem mass spectrometry (MS/MS) data plays the key role in the characterization of novel protein sequences. This field has been studied over the past 20 years and a number of de novo sequencing tools have been proposed such as PepNovo™, PEAKS™, NovoHMM™, MSNovo™, pNovo™, UniNovo™, Novor™ among others [6-19]. The recent "gold rush" into monoclonal antibodies has elevated the application of de novo sequencing to a new horizon [20-23]. Yet computational challenges still remain as MS/MS spectra contain much noise and ambiguity that requires rigorous global optimization with various forms of dynamic programming that have been developed over the past decade [8-10,12,13,15-19,24].

Monoclonal antibodies play important roles in therapeutic strategies due to their mechanisms of variations. However, it is such variations that also defied many attempts at developing an automated system to sequence them. Each monoclonal antibody (mAb) sequence is a novel protein that requires de novo sequencing with no resembling proteins (for the variable regions) in the databases.

SUMMARY OF THE INVENTION

In accordance with an aspect of the present invention, there is provided a computer implemented system for de novo sequencing of peptides from mass spectrometry data using neural networks, the computer implemented system comprising: a processor and at least one memory providing a plurality of layered nodes configured to form an artificial neural network for generating a probability measure for one or more candidates to a next amino acid in an amino acid sequence, the artificial neural network trained on known mass spectrometry spectrum data containing a plurality of known fragment ions peaks of known sequences differing in length and differing by one or more amino acids; wherein the plurality of layered nodes receives a mass spectrometry spectrum data as input, the plurality of layered nodes comprising: at least one convolutional layer for filtering mass spectrometry spectrum data to detect fragment ion peaks; and the processor configured to: obtain an input prefix representing a determined amino acid sequence of the peptide, identify a next amino acid based on a candidate next amino acid having a greatest probability measure based on the output of the artificial neural network and the mass spectrometry spectrum data of the peptide; and update the determined amino acid sequence with the next amino acid.

In one embodiment, there is provided the system described herein, wherein the plurality of layered nodes comprise at least one fully-connected layer for identifying pairs of: a) a fragment ion peak corresponding to a sequence that is one amino acid longer than the determined amino acid sequence, and b) a fragment ion peak corresponding to a sequence that is one amino acid less than the remaining undetermined amino acid sequence of the peptide, by fitting the plurality of known fragment ions peaks against the mass spectrometry spectrum data, and for outputting the probability measure for each candidate next amino acid.

In one embodiment, there is provided the system described herein, comprising a mass spectrometer configured to generate a mass spectrometry spectrum data of a peptide.

In one embodiment, there is provided the system described herein, wherein the plurality of layered nodes receives an image data or a vector data representing the mass spectrometry spectrum data as input, and output a probability measure vector.

In one embodiment, there is provided the system described herein, wherein the processor is configured to determine the entire sequence of the peptide by obtaining the probability measures of candidates at a number of points in the sequence and beam searching.

In one embodiment, there is provided the system described herein, wherein the plurality of layered nodes comprise a first convolutional layer for applying one or more filters to the mass spectrometry spectrum data using a 4-dimensional kernel and a bias term.

In one embodiment, there is provided the system described herein, wherein the plurality of layered nodes comprise a second convolutional layer for applying further one or more filters using an additional 4-dimensional kernel.

In one embodiment, there is provided the system described herein, wherein the plurality of layered nodes comprise a first fully-connected layer having as many neuron units as there are outputs from the at least one convolutional layer, and a second fully-connected layer comprising as many neuron units as there are possible entries for the next amino acid.

In one embodiment, there is provided the system described herein, wherein a first dropout is applied after the first convolutional layer.

In one embodiment, there is provided the system described herein, wherein a second dropout is applied after the second convolutional layer.

In one embodiment, there is provided the system described herein, wherein the system is configured to bi-directionally sequence the peptide using two separate sets of parameters, wherein one set comprises parameters for forward sequencing and the other set comprises parameters for backward sequencing.

In one embodiment, there is provided the system described herein, wherein a pair of fragment ion peaks are filtered out when the sum of: a mass corresponding to the fragment ion peak of a), and a mass corresponding to the fragment ion peak of b) exceed the total mass of the peptide.

In one embodiment, there is provided the system described herein, wherein the artificial neural network is further trained on a database of known peptide sequences; and wherein the plurality of layered nodes comprise: one or more layers comprising a convolutional neural network (CNN) for identifying the presence of amino acids in the mass spectrometry spectrum data and generate one or more output vectors representing a list of amino acids present in the peptide; and one or more layers comprising a recurrent neural network (RNN) for predicting the next amino acid by vector embedding the one or more output vectors, and for outputting the probability measure for each candidate next amino acid.

In one embodiment, there is provided the system described herein, wherein the processor is configured to convert the mass spectrometry spectrum data into an intensity vector listing an intensity value for each mass range over the mass spectrometry spectrum data.

In one embodiment, there is provided the system described herein, wherein the processor is configured to: slice the intensity vector by subdividing the mass ranges, such that the sliced intensity vector lists intensity values for mass ranges corresponding to multiples of the mass of an amino acid, and generate an input array comprising a plurality of sliced intensity vectors each corresponding to a different amino acid.

In one embodiment, there is provided the system described herein, wherein the one or more layers of the plurality of layered nodes comprising the RNN is a long short-term memory network (LSTM).

In one embodiment, there is provided the system described herein, wherein the one or more layers of the plurality of layered nodes comprising the LSTM comprises 2 or 3 layers.

In one embodiment, there is provided the system described herein, wherein the one or more layers of the plurality of layered nodes comprising the LSTM comprise a last fully-connected layer having as many neuron units as there are possible entries for the next amino acid.

In one embodiment, there is provided the system described herein, wherein the one or more layers of the LSTM is for predicting the next amino acid by embedding the output vector to form a two-dimensional array by iterating according to the following equation, $x_0 = CNN_{spectrum}(I)$ $x_{t-1} = Embedding_{a_{t-1},*}, t>1$ $s_t = LSTM(x_{t-1})$ where I is the spectrum intensity vector, a(t−1) is the symbol predicted at iteration t−1, Embedding(i,*) is the row i of the embedding array, and st is the output of the LSTM and will be used to predict the symbol at iteration t.

In one embodiment, there is provided the system described herein, wherein the one or more layers comprising the CNN is for identifying the presence of amino acids in the mass spectrometry spectrum data by fitting known single or multiple amino acid long fragment ion peaks to the mass spectrometry spectrum data.

In one embodiment, there is provided the system described herein, wherein the one or more layers comprising the CNN is for identifying the presence of amino acids in the mass spectrometry spectrum data by identifying two fragment ion peaks that differ by one amino acid.

In accordance with an aspect of the present invention, there is provided a computer implemented system for de novo sequencing of peptides from mass spectrometry data using neural networks, the computer implemented system comprising: a processor and at least one memory providing a plurality of layered nodes configured to form an artificial neural network for generating a probability measure for one or more candidates to a next amino acid in an amino acid sequence, the artificial neural network trained on: known mass spectrometry spectrum data containing a plurality of known fragment ions of known sequences differing in length and differing by one or more amino acids, and a database of known peptide sequences; wherein the plurality of layered nodes receives a mass spectrometry spectrum data as input, the plurality of layered nodes comprising a first set of layered nodes and a second set of layered nodes; wherein the first set of layered nodes comprises: at least one convolutional layer for filtering mass spectrometry spectrum data to detect fragment ion peaks; and at least one fully-connected layer for identifying pairs of: a) a fragment ion peak corresponding to a sequence that is one amino acid longer than the determined amino acid sequence, and b) a fragment ion peak corresponding to a sequence that is one amino acid less than the remaining undetermined amino acid sequence of the peptide, by fitting the plurality of known fragment ions peaks against the mass spectrometry spectrum data; wherein the second set of layered nodes comprises: one or more layers comprising a convolutional neural network (CNN) for identifying the presence of amino acids in the mass spectrometry spectrum data and generate one or more output vectors representing a list of amino acids present in the peptide; and one or more layers comprising a recurrent neural network (RNN) for predicting the next amino acid by vector embedding the one or more output vectors; wherein the first and second set of layered nodes share at least one common last fully-connected layer for outputting the probability measure for each candidate next amino acid; the processor configured to: obtain an input prefix representing a determined amino acid sequence of the peptide, identify a next amino acid based on a candidate next amino acid having a greatest probability measure based on the output of the artificial neural network and the mass spectrometry spectrum data of the peptide; and update the determined amino acid sequence with the next amino acid.

In one embodiment, there is provided the system described herein, wherein the first and second neural networks share a first and a second common last fully-connected layer, wherein the first common last fully-connected layer is for concatenating the outputs from the first and second neural networks, and the second fully-connected layer comprises as many neuron units as there are possible candidates the next amino acid.

In accordance with an aspect of the present invention, there is provided a method for de novo sequencing of peptides from mass spectrometry data using neural networks, the method comprising: obtaining a mass spectrometry spectrum data of a peptide; filtering the mass spectrometry spectrum data to detect fragment ion peaks by at least one convolutional layer of a plurality of layered nodes configured to form an artificial neural network for generating a probability measure for one or more candidates to a next amino acid in an amino acid sequence; outputting a probability measure for each candidate of a next amino acid; obtaining an input prefix representing a determined amino acid sequence of the peptide; identifying a next amino acid based on a candidate next amino acid having a greatest probability measure based on the output of the artificial neural network and the mass spectrometry spectrum data of the peptide; and updating the determined amino acid sequence with the next amino acid.

In one embodiment, there is provided the method described herein, comprising fitting a plurality of known fragment ions peaks of known sequences against the mass spectrometry spectrum data to identifying pairs of: a) a fragment ion peak corresponding to a sequence that is one amino acid longer than the determined amino acid sequence, and b) a fragment ion peak corresponding to a sequence that is one amino acid less than the remaining undetermined amino acid sequence of the peptide, by at least one fully-connected layer of the plurality of layered nodes.

In one embodiment, there is provided the method described herein, wherein the known fragment ion peaks of known sequences differ in length and differ by one or more amino acids, and wherein the method comprises training the artificial neural network on the known fragment ion peaks.

In one embodiment, there is provided the method described herein, comprising filtering out a pair of fragment ion peaks when the sum of: a mass corresponding to the fragment ion peak of a), and a mass corresponding to the fragment ion peak of b) exceed the total mass of the peptide.

In one embodiment, there is provided the method described herein, comprising: identifying the presence of amino acids in the mass spectrometry spectrum data by one or more layers of the plurality of layered nodes comprising a convolutional neural network; generating one or more output vectors representing a list of amino acids present in the peptide; predicting a next amino acid by vector embedding the one or more output vectors by one or more layers of the plurality of layered nodes comprising a recurrent neural network.

In one embodiment, there is provided the method described herein, comprising converting the mass spectrometry spectrum data into an intensity vector listing an intensity value for each mass range over the mass spectrometry spectrum data.

In one embodiment, there is provided the method described herein, comprising training the plurality of layered nodes on: known mass spectrometry spectrum data containing a plurality of known fragment ions of known sequences differing in length and differing by one or more amino acids, and a database of known peptide sequences.

In one embodiment, there is provided the method described herein, comprising identifying the presence of amino acids in the mass spectrometry spectrum data by fitting known single or multiple amino acid long fragment ion peaks to the mass spectrometry spectrum data.

In one embodiment, there is provided the method described herein, comprising identifying the presence of amino acids in the mass spectrometry spectrum data by identifying two fragment ion peaks that differ by one amino acid.

In one embodiment, there is provided the method described herein, comprising converting the mass spectrometry spectrum data into an intensity vector listing intensity values for mass ranges over the mass spectrometry spectrum data, and the plurality of layered nodes receives the intensity vector as input and output a probability measure vector.

In one embodiment, there is provided the method described herein, comprising slicing the intensity vector by subdividing the mass ranges, such that the sliced intensity vector lists intensity values for mass ranges corresponding to multiples of the mass of an amino acid, and generating an input array comprising a plurality of sliced intensity vectors each corresponding to a different amino acid.

BRIEF DESCRIPTION OF THE FIGURES

Embodiments of the invention may best be understood by referring to the following description and accompanying drawings. In the drawings:

FIG. 7A. Precision-recall curves on V.mungo. FIG. 7B. Precision-recall curves on M.musculus. FIG. 7C. Precision-recall curves on M.mazei. FIG. 7D. Precision-recall curves on Bacillus. FIG. 7E. Precision-recall curves on C.endoloripes. FIG. 7F. Precision-recall curves on S.lycopersicum. FIG. 7G. Precision-recall curves on S.cerevisiae. FIG. 7H. Precision-recall curves on A.mellifera. FIG. 7I. Precision-recall curves on H.sapiens.

FIG. 8A. Recall at amino acid level. FIG. 8B. Precision at amino acid level. FIG. 8C. Recall at peptide level.

DETAILED DESCRIPTION

Figure 1:
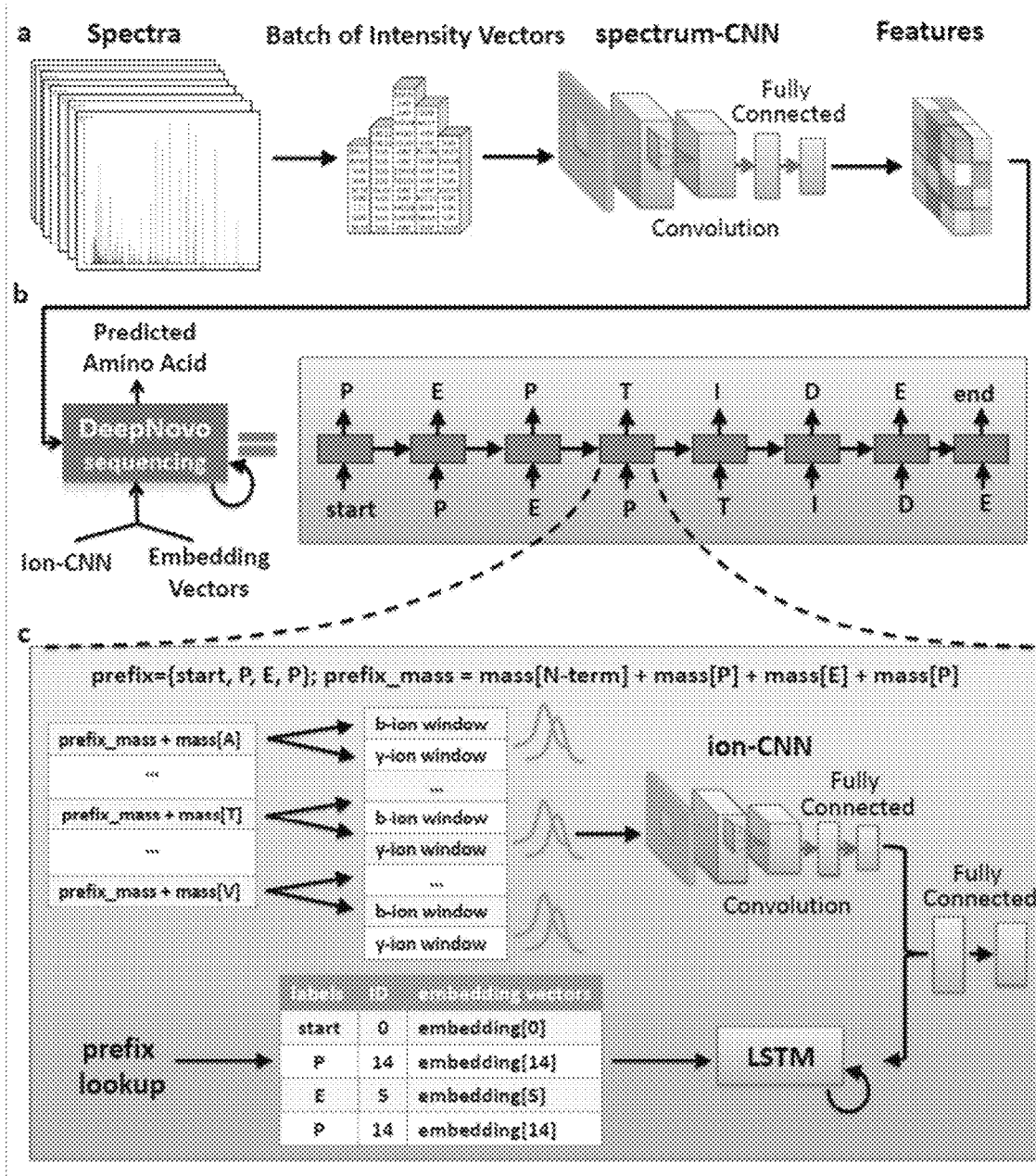
FIG. 1 shows an embodiment of the system described herein, named DeepNovo for de novo peptide sequencing. a. Spectra are processed by the convolutional neural network spectrum-CNN and then used to initialize the LSTM network. b. DeepNovo sequences a peptide by predicting one amino acid at each iteration. Beginning with a special symbol "start", the model predicts the next amino acid by conditioning on the input spectrum and the output of previous steps. The process stops if in the current step the model outputs the special symbol "end". c. Details of a sequencing step in DeepNovo. Two classification models, ion-CNN and LSTM, use the output of previous sequencing steps as a prefix to predict the next amino acid.

De novo peptide sequencing from tandem mass spectrometry data is one technology in proteomics for the characterization of proteins, especially for new sequences such as monoclonal antibodies. The present inventors have developed a system that utilizes neural networks and deep learning to perform de novo peptide sequencing, and at the same time introduced a number of improvement to the process of de novo peptide sequencing.

As used herein, "de novo peptide sequencing" refers to a method in which a peptide amino acid sequence is determined from raw mass spectrometry data. De novo sequencing is an assignment of peptide fragment ions from a mass spectrum. In a mass spectrum, an amino acid is determined by two fragment ions having a mass difference that corresponds to an amino acid. This mass difference is represented by the distance between two fragment ion peaks in a mass spectrum, which approximately equals the mass of the amino acid. In some embodiments, de novo sequencing systems apply various forms of dynamic programming approaches to select fragment ions and predict the amino acids. The dynamic programming approaches also take into account constrains, for example that a predicted amino acid sequence must have corresponding mass.

Deep learning is used in a number of research fields [25], such as image processing [26,27], speech recognition [28], and natural language processing [29]. One example of deep learning application in biological sciences [30], for instance, in the field of genomics is deep neural network models for predicting the effects of noncoding single-nucleotide variants [31], predicting protein DNA- and RNA-binding sites [32], protein contact map prediction [33], and mass spectrometry imaging [46].

As used herein, "deep learning" refers to the application to learning tasks of artificial neural networks (ANNs) that contain more than one hidden layer. Deep learning is part of a broader family of machine learning methods based on learning data representations, as opposed to task specific algorithms. One key aspect of deep learning is its ability to learn multiple levels of representation of high-dimensional data through its many layers of neurons. Furthermore, unlike traditional machine learning methods, those feature layers are not pre-designed based on domain-specific knowledge and hence they have more flexibility to discover complex structures of the data.

The present inventors have developed a system using artificial neural networks in de novo peptide sequencing from mass spectrum data. Mass spectrum data presents an unique set of challenges, in that it is difficult to process due to the high level of background noise and ambiguity in terms of detecting signals. The task of de novo peptide sequencing is to reconstruct the amino acid sequence of a peptide starting with a mass spectrum and in some embodiments the peptide mass is also provided. In other embodiments, the peptide mass is determined using known processes, and the sequence is determined using de novo sequencing.

As shown in FIG. 1 (see a), a tandem mass spectrum is often presented as a histogram-plot of intensity versus mass (more precisely, mass-to-charge ratio, or m/z) of the ions acquired from the peptide fragmentation inside a mass spectrometer. The underlying raw format (e.g. mgf) is a list of pairs of mass and intensity. In the present systems and methods, a spectrum is discretized into a vector, called an intensity vector. In some embodiments, the intensity vectors are indexed such that masses correspond to indices and intensities are values. This representation assumes a maximum mass and also depends on a mass resolution parameter. For instance, if the maximum mass is 5,000 Dalton (Da) and the resolution is 0.1 Da, then the vector size is 50,000 and every 1-Dalton mass is represented by 10 bins in the vector. In one embodiment, two types of data are considered: low-resolution (0.1 Da) and high-resolution (0.01 Da). High-resolution data often allow de novo peptide sequencing tools to achieve better accuracy.

In some cases, the challenges facing de novo sequencing can be appreciated as a challenge of automatically generating a description for an image. In one research, a convolutional neural network (CNN), i.e. a type of feed-forward artificial neural network consisting of multiple layers of receptive fields, is used to encode, or to "understand", an image. Then, a long short-term memory (LSTM) recurrent neural network (RNN) [34] is used to decode, or to "describe", the content of the image [35,36]. That research tries to connect image recognition and natural language processing by integrating two fundamental types of neural networks, CNN and LSTM.

For de novo sequencing, the present systems and methods described herein applies image recognition and description to mass spectrometry data, which requires a different set of parameters and approach compared to known image recognition. For de novo sequencing, exactly one out of $20^L$ amino acid sequences can be considered as the correct prediction (L is the peptide length, 20 is the total number of possible amino acids). Another challenge to de novo sequencing from mass spectrometry data is that peptide fragmentation generates multiple types of ions including a, b, c, x, y, z, internal cleavage and immonium ions [48]. Depending on the fragmentation methods, different types of ions may have quite different intensity values (peak heights), and yet, the ion type information remains unknown from spectrum data.

Furthermore, there are plenty of noise peaks mixing together with the real ions. Finally, the predicted amino acid sequence should have its total mass approximately equal to the given peptide mass. This points to a complicated problem of pattern recognition and global optimization on noisy and incomplete data. In some embodiments, this issue is handled by global dynamic programming [8-10,12,13,15-19,24], divide-and-conquer [11] or integer linear programming [14]. However, there is no naïve application of existing deep learning architectures that work directly on this problem of optimizing de novo sequencing from noisy and incomplete data.

Accordingly, the present inventors have developed systems that allow for deep learning to be applied in de novo peptide sequencing. In some embodiments, adopting neural networks in systems for de novo peptide sequencing allows for greater accuracy of reconstructing peptide sequences. Systems incorporating neural networks also allows for greater coverage in terms of peptides that can be sequenced by de novo peptide sequencing. As well, in some embodiments, access to external databases are not needed.

In one embodiment, a deep learning system is provided for de novo peptide sequencing. The system combines convolutional neural networks (CNNs) and recurrent neural networks (RNNs) to learn features of tandem mass spectra, fragment ions, and sequence patterns of peptides. The networks are further integrated with local dynamic programming to solve the complex optimization task of de novo sequencing. In some embodiments, the system performed better than existing de novo sequencing algorithms by a large margin of 7.7 to 22.9% at the amino acid level and 38.1 to 64.0% at the peptide level. In one embodiment, the system automatically reconstruct the complete sequences of the light and heavy chains of a mouse antibody, achieving 97.5% to 100% coverage and 97.2 to 99.5% accuracy, without using assisting databases. (See for example FIG. 2)

In some embodiments, the system takes advantage of high-performance computing CPUs and massive amount of data to offer a complete end-to-end training and prediction solution. The CNN and LSTM networks of the system can be jointly trained from scratch given a set of annotated spectra obtained from spectral libraries or database search tools. This allows the system to be trained by both general and specific models to adapt to various sources of data. In one embodiment, the system further automatically reconstructs the complete sequences of antibodies, such as the light and heavy chains of an antibody. Determining the sequences of antibodies, including novel antibodies, is one application of peptide sequencing and the present systems and methods. Antibody sequencing previously required de novo sequencing, database search, and homology search together to succeed [21]. An example of antibody sequencing systems and methods are disclosed in U.S. patent application Ser. No. 15/599,431, the entire content of which is hereby incorporated by reference. The present systems and methods do not require a database search or homology search.

Moreover, the system is re-trainable to adapt to various sources of data and in some embodiments provides a complete end-to-end training and prediction solution to the de novo sequencing problem.

In some embodiments, the system solves optimization problems by utilizing deep learning and dynamic programming. In some embodiments, the system comprises a processor, such as a central processing unit (CPU) or graphics processing unit (GPU). Preferably, the system comprises a GPU.

Mass Spectrometry

In some embodiments, the system comprises a mass spectrometer, examples of which include: tandem mass spectrometer (MS/MS) and liquid chromatography tandem mass spectrometer (LC-MS/MS). LC-MS/MS combines liquid chromatography with a tandem mass spectrometer. Mass spectrometry (MS) is an analytical technique that ionizes chemical species and sorts the ions based on their mass-to-charge ratio. MS can be applied to pure samples as well as complex mixtures. In an example MS procedure, a sample, which may be solid, liquid, or gas, is ionized, for example, by bombarding it with electrons. This causes some of the sample's molecules to break into charged fragments of various sizes and masses. For example, a 10 amino acid length peptide is fragmented between the $3^{rd}$ and $4^{th}$ amino acid, resulting in one fragment of 3 amino acids long and another fragment of 7 amino acids long. These are also referred to as b- and y-ions. These ions are then separated according to their mass-to-charge ratio and detected. The detected ions are displayed as a mass spectra of the relative abundance of detected ions as a function of the mass-to-charge ratio.

As used herein, "b-fragment ion" refers to fragment peaks on tandem mass spectrum resulting from peptide fragments extending from the amino terminus of the peptide; while "y-fragment ion" refers to fragment peaks from peptide fragments extending from the C-terminus of the peptide. In some embodiments, determining peptide sequences from the amino terminus of the peptide is referred to as the forward direction, while determining peptide sequences from the C-terminus of the peptide is referred to as the backward direction.

The overall process for mass spectrometry includes a number of steps, specifically, the ionization of the peptides, acquisition of a full spectrum (survey scan) and selection of specific precursor ions to be fragmented, fragmentation, and acquisition of MS/MS spectra (product-ion spectra). The data is processed to either quantify the different species and/or determine the peptide amino acid sequence. Since the number of ion populations generated by MS exceeds that which contemporary instruments can individually target for sequence analysis with a tandem mass spectrum scan, it is often necessary to control the data acquisition process and manage the limited scan speed. Data-dependent acquisition (DDA) performs a precursor scan to determine the mass-to-charge ratio (m/z) and abundance of ions currently entering the mass spectrometer, followed by sequence determining MS/MS scans on ions from a subset of detected peaks.

Mass spectrometry data is stored, for example, as a mass spectra or a plot of the ion signal as a function of the mass-to-charge ratio, a data table listing ion signal and related mass-to-charge ratio, a data string comprising pairs of ion signal and related mass-to-charge ratio, where values can be stored in corresponding data fields and data instances. The mass spectra data sets may be stored in various data structures for retrieval, transformation, and modification. Such data structures can be, for example, one or more tables, images, graphs, strings, maps, linked lists, arrays, other data structure, or a combination of same.

In preferred embodiments of the system, the mass spectrometry data or mass spectra are converted into intensity vectors indexed such that mass ranges correspond to indices and intensities are values. For example, the intensity vectors are indexed as follows:

Intensity vector=$(I_{(mass=0-0.1Da)}, I_{(mass=0.1-0.2Da)}, I_{(mass=0.2-0.3Da)}, \ldots, I_{(mass=(max-0.1Da)-max)})$ where "I" is the intensity value as read from the y-axis of mass spectra, for each mass range (or m/z value) taken from the x-axis of the mass spectra. "Da" is the unit, Daltons.

In some embodiments, each mass range is 1 to 0.00001 Da. In preferred embodiments, each mass ranges is 0.1 to 0.01 Da.

Neural Network

In some embodiments, a processor and at least one memory provides a plurality of layered nodes to form an artificial neural network. The process is configured to determine the amino acid sequence of a peptide.

In some embodiments, the system comprises a neural network. The system receives a sequence that has been predicted up to the current iteration or position in the peptide sequence and outputs a probability measure for each of the next possible element in the sequence by interpreting the fragment ion peaks of the mass spectra. In one embodiment, the system iterates the process until the entire sequence of the peptide is determined.

In one embodiment, the neural network is a convolutional neural network (CNN). In another embodiment, the neural network is a recurrent neural network (RNN), preferably a long short-term memory (LSTM) network. In yet another embodiment, the system comprises a CNN and a RNN arranged in series, for first encoding the intensity vectors from mass spectra into feature vectors and then predict the next element in the sequence in a manner similar to predictive text (for predicting the next word in a sentence based on the context of other words and the first letter typed). In one preferred embodiment, the system comprises both a CNN and a RNN arranged in parallel. In some embodiments, the system comprises one or more CNNs and one or more RNNs.

As used herein, a "prefix" refers to a sequence of amino acids that have been predicted up to the current iteration. In some embodiments, a prefix includes a "start" symbol. In one preferred embodiment, a fully sequenced peptide sequence begins with the "start" symbol and ends with an "end" symbol. The prefix is indexed, for example, using the single-letter representation of amino acids or the amino acid name. Using the example from FIG. 1 (see c), a prefix is indexed as:

prefix={start,$P,E,P$} and the mass of this prefix ("prefix mass") is indexed as:

prefix_mass=mass[$N$-term]+mass[$P$]+mass[$E$]+mass[$P$]

CNN

In embodiments of the system comprising a CNN, the CNN comprises a plurality of layers. In some embodiments, the CNN comprises at least one convolutional layer and at least one fully connected layer. In some embodiments, the CNN comprises one convolutional layer and two fully connected layers. In other embodiments, the CNN comprises two convolutional layers and one fully connected layer. In preferred embodiments, the CNN comprises 2 convolutional layers and 2 fully connected layers. In other embodiments, the CNN comprises a different combination and/or quantity of convolutional layer(s) and connected layer(s). A convolutional layer applies a convolution operation to the input, passing the result to the next layer; while fully connected layers connect every neuron in one layer to every neuron in another layer.

The inventors have found that adding a second convolutional layer to the first convolutional layer, as well as adding a second fully connected layer to the first connected layer, both significantly increased the accuracy of the system. Adding further convolutional layers or fully connected layers beyond the first two in both cases may yield greater accuracy but these increases in accuracy were not significant. Instead, having more than two convolutional layers or two fully connected layers increased the computational and processing burden of the system, thereby increasing the demand for processing power needed for the system to operate.

In some embodiments, the first convolution layer is configured to detect the fragment ion peaks of a mass spectrum by image processing, wherein the mass spectra data is stored as, for example, intensity vectors as described above. As used herein, in image processing, a kernel, convolution matrix, or mask is a small matrix, which is used for blurring, sharpening, embossing, edge detection, and more. For example, this is accomplished by performing a convolution between a kernel and an image (such as a mass spectra), which is the process of adding each element of the image to its local neighbors, weighted by the kernel. The fragment intensity peaks of a mass spectrum can be characterized as a bell curve, and the first convolutional layer is configured to capture or detect the shape of the bell curve by fitting or applying mask filters sized according to the kernel used.

In some embodiments, the system further comprises a Rectified Linear Unit (ReLU) to add nonlinearity to the neural network. The ReLU is configured to capture the curvature of the bell curve.

In further embodiments, the system further applies dropout to a layer. As used herein "dropout" is a regularization technique for reducing overfitting in neural networks by preventing complex co-adaptations on training data. To apply dropout, neuron units are randomly activated (or dropped) at every training iteration so that they do not co-adapt. In one embodiment, the dropout probability for a convolutional layer is 0%-25%, preferably 25%. In another embodiment, the dropout probability for a fully connected layer is 0%-50%, preferably 50%.

In some embodiments, ReLU is applied to each convolutional and/or fully connected layer. In other embodiments, dropout is applied to each convolutional and/or fully connected layer. In preferred embodiments, ReLU and dropout are applied to each convolutional and/or fully connected layer.

In preferred embodiments, a second convolutional layer is applied on top of the first convolutional layer. The second convolution layer is similar in configuration to the first convolutional layer, and is configured to apply a second fitting of filters on top of the first. The second convolutional layer differs from the first in that it uses a finer filter with a smaller window size to more finely capture the bell curve shape of the fragment ion peaks of a mass spectrum.

The convolutional layers are followed by fully-connected layers (also known as hidden layers). In some embodiments, where the CNN comprises two fully-connected layers, the first fully-connected layer comprises 128-2000 neuron units. In one embodiment, the first fully-connected layer comprises 128-250 neuron units or 1000-2000 neuron units. In preferred embodiments, the first fully-connected layer comprises 512 neuron units, to maximize accuracy of the system while at the same time minimizing the processing power needed by the system.

Given a prefix input, the CNN is used for detecting particular fragment ions in the mass spectrum. In one embodiment, a fully-connected layer is configured to fit known fragment ions to the mass spectrum. In one preferred embodiment, the first fully-connected layer is configured to identify the next possible amino acid by fitting the corresponding b- and y-ions to the mass spectrum image. In another preferred embodiment, by fitting b- and y-ions corresponding to the next amino acid to be determined in a peptide sequence. This method is also outlined in FIG. 1 (see c). For example, given a 10 amino acid long peptide and a prefix input comprising the first 3 amino acids from the amino end of the peptide that has already been determined, the system iteratively goes through each of the 20 possible amino acids to identify candidate 4th amino acid for this peptide. Using the example of Alanine as the 4th amino acid, the mass of the prefix and the 4th amino acid Alanine is determined. Since a mass spectrum involves the fragmentation of peptides, for a 4 amino acid long fragment from the amino end of the peptide, there is a corresponding 6 amino acid long fragment from the C-end of the peptide, using this example. These two fragments are called b-ions and y-ions. The first fully-connected layer is configured to take these b-ions and y-ions for each candidate next amino acid in the sequence and fits the b-ions and y-ions against the mass spectrum. Matches with fragment peaks in the mass spectrum means that these b-ions and y-ions are present in the fragments generated by the mass spectrum, and in turn more likely that the candidate amino acid is the next one in the sequence.

In some embodiments, the CNN is trained on one or more mass spectra of one or more known peptides. In other embodiments, the CNN is trained on one or more mass spectra with ion peaks corresponding to known peptide fragments. These known peptide fragments have varying lengths and sequences. In some embodiments, these known peptide fragments vary by one amino acid residue in length. In one embodiments, for each set of known peptide fragments of the same length, they each vary by one amino acid at a particular location. In yet other embodiments, these known rometry. Biochemistry 26, 1209-1214 (1987).

2. Marin Some Embodiments, the Last Fully-Connected Layer has as Many Neuron Units In some embodiments, the last fully-connected layer has as many neuron units as the number different possible elements for a sequence. For example, the last fully-connected layer may have at least 20 neuron units, based on the 20 possible amino acids. In one embodiment, the last fully-connected layer has 26 neuron units corresponding to 26 possible symbols or elements to predict from. The 26 symbols refers to "start", "end", "padding", the 20 possible amino acids, three amino acid modifications (for example: carbamidomethylation (C), Oxidation (M), and Deamidation (NQ)) for a total of 26. The "padding" symbol refers to blanks.

The output from the final fully-connected layer is a probability measure for each of the next possible element in the sequence. This output is stored as, for example, data tables, vectors, data arrays, or data strings comprising pairs of candidate amino acid and the corresponding probability, where values can be stored in corresponding data fields and data instances. For example, given an input prefix comprising the first three predicted amino acids, the output for the $4^{th}$ candidate amino acid is indexes as a probability vector: [(Alanine, 80%), (Arginine, 15%), (Asparagine, 5%)]. In some embodiments, the output is a probability distribution, summing up to a total of 100%.

In some embodiments, a filter or set of filters (for example, in the first convolutional layer) are applied to image data or processed image data (for example, a data representation of a mass spectra image or portion of same such as a peak) to identify features that the CNN has been trained to recognize as corresponding to a b-ion or y-ion containing a particular amino acid at a particular location in an original peptide sequence. In these embodiments, the CNN is configured to use an additional filter or sets of filters to identify features that the CNN has been trained to recognize as corresponding to a b-ion or y-ion containing a particular amino acid at a particular location of the original peptide sequence, for each of the other possible amino acids at each of the other possible locations in the original peptide sequence. In some embodiments, the fully connected layer of the CNN outputs a probability vector that the original mass spectrometry image, portion thereof, or data representation of same contains each of the possible amino acids at the specific sequence location. The CNN can then be used to generate a probability vector of the original mass spectrometry image, portion thereof, or data representation of same for each of the other sequence locations. In this way, in some embodiments, the CNN is used to predict the amino acid sequence of a peptide based on mass spectrometry data of b-ions and y-ions or other peptide fragments.

In preferred embodiments, the final output of the system is a vector of 26 signals, or logits vector (unscaled log probabilities), corresponding to the probability of each of the 26 possible symbols being the next element in the sequence. To identify the next amino acid in a peptide sequence, the amino acid or symbol with the highest probability is chosen.

RNN

In one embodiment comprising a RNN, the system comprises a spectrum-CNN connected to a RNN. The RNN is preferably a LSTM, In one embodiment, the spectrum-CNN or the system is configured to encode the intensity vectors from mass spectra into "feature vectors", before the features vectors are inputted into a LSTM network. In some embodiments, the spectrum-CNN determines the present of individual amino acids present in a peptide by identifying fragment ion peaks corresponding to individual amino acids. In one embodiment, the spectrum-CNN determines the presence of individual amino acids or short segments of amino acid sequences by identifying corresponding fragment ion peaks. In preferred embodiments, the specrtrum-CNN determines the present of individual amino acids present in a peptide by identifying fragment ion peaks that differ by one amino acid and calculating the mass difference between the two fragment ion peaks.

In some embodiments, the spectrum-CNN comprises one or more convolutional layers, preferably two layers, and one or more fully-connected layers. In some embodiments, the spectrum-CNN is configured in the same manner as the CNN embodiments described above, except to the extent of predicting the next amino acid in the sequence. In preferred embodiments, the system is configured to first slice each input intensity vector into pieces based on the amino acid masses. For example, the mass of Alanine, or "A", is 71.0 Da and if the intensity vector has mass ranges of 0.1 Da, the intensity vector is sliced by every index of 710 until the end, converting the intensity vector into a feature vector indexed for example as:

$$\text{Feature vector} = (I_{(mass=0-aa)}, I_{(mass=aax1-aax2)}, I_{(mass=aax2-aax3)}, \ldots)$$

where "aa" refers to amino acid. This procedure is repeated for each possible symbol or element. For example, in the case of 20 amino acids, each intensity vector is sliced into 20 feature vectors. The sliced vectors are inputted through the spectrum-CNN, and outputted as a vector of a size corresponding to the number of neuron units of the last fully-connected layer. In one embodiment, the spectrum-CNN comprises one fully-connected layer of, for example, 512 neuron units and therefore outputs a vector of size 512.

The output from the spectrum-CNN is input into a LSTM. In some embodiments, the output from the spectrum-CNN is a vector or array listing the amino acids present in a peptide. In one embodiment, the output from the spectrum-CNN is a vector or array listing the amino acid identity and number of said amino acid in a peptide.

The architectural configuration of a LSTM is known to a skilled person, for example as described in reference [34], the entire content of which is incorporated herein by reference. In some embodiments, the LSTM comprises at least one layer. In preferred embodiments, the LSTM comprises 2 or 3 layers. In other embodiments, each layer comprises 128-2000 neuron units, preferably, 512 neuron units. The LSTM is configured to embed the inputted vectors (such as the vector of size 512) to represent each of the, for example, 26 symbols into a 2-dimensional array. The system iteratively inputs the vector of size 512 through the LSTM, with the first iteration of vector of size 512 being the output from the spectrum-CNN, and outputs a predicted candidate next amino acid in the sequence.

In other embodiments, the LSTM is configured to embed the inputted vectors according to the systems and procedures described in U.S. patent application Ser. No. 15/599,431, publication no. US20170336419A1, titled METHODS AND SYSTEMS FOR ASSEMBLY OF PROTEIN SEQUENCES, the entire content of which is incorporated herein by reference.

In some embodiments, the LSTM further comprises a last fully-connected layer of 26 neuron units, or as many neuron units as there are possible elements at a given position in a sequence, to perform a linear transformation of the vector of 512 output into signals of 26 symbols to predict. In one embodiment, the output from the last fully-connected layer is a probability measure for each of the possible 26 symbols.

CNN and RNN

In some embodiments where the system comprises both a CNN and a RNN in parallel, the system first concatenates or links the outputs of each respective second-to-last layers (for example, second last fully-connected layer of the CNN and the second last layer of the LSTM). Using the above examples, where the second last fully-connected layer of the CNN has 512 neuron unit yielding a vector of size 512, and the second last layer of the LSTM also yields a vector of size 512, these two vectors are combined into a vector of size 1024. In one embodiment, the system further adds on a fully-connected layer having a number of neuron units corresponding to the size of the combined vector (for example, combined vector of size 1024 above). In preferred embodiments, the system further applies ReLU activation and dropout as described above. Lastly, the system further adds another fully-connected layer of as many neuron units as there are possible elements at a given position in a sequence (for example, 26 neuron units), to yield an output of probability measures of each of the candidate next amino acid.

In preferred embodiments, the final output of the system is a vector of 26 signals, or logits vector (unscaled log probabilities), corresponding to the probability of each of the 26 possible symbols being the next element in the sequence. To identify the next amino acid in a peptide sequence, the amino acid or symbol with the highest probability is chosen.

Other Embodiments

In one preferred embodiment, while selecting the next amino acid, the system is configured to calculate the suffix mass and employs knapsack dynamic programming to filter out those amino acids whose masses do not fit the suffix mass. As used herein, "suffix mass" refers to the sum total mass of the amino acids remaining to be predicted. The prefix mass and the suffix mass must add up to equal the total mass of the peptide that is being sequenced. In embodiments where knapsack is applied to filter out amino acids whose masses do not fit the suffix mass; the recall and/or accuracy of the system were increased (see for example FIG. 4).

In preferred embodiments, the system performs bi-directional sequencing and uses two separate sets of parameters, forward (for example, sequencing from the amino end of the peptide) and backward (for example, sequencing from the carboxylic end of the peptide), for the CNN. This is not done for the spectrum-CNN and the embedding vectors. The present inventors have found that embodiments of the system that perform bi-directional sequencing achieves better accuracy than using only one direction.

In most preferred embodiments, the system is configured to predict the next amino acids using a beam search to optimize the prediction. As used herein "beam search" refers to a heuristic search where instead of predicting the next element in a sequence one at a time at each iteration based on probability, the next n-elements are predicted based on the overall probability of the n-elements. For example, where n=5, the system predicts the next 5 amino acids at a time in the sequence at each iteration based on the an overall probably of the next 5 candidate amino acids sequences which is derived from the product of each individual amino acid probabilities.

In some embodiments, there is provided a computer implemented system for de novo sequencing of peptides from mass spectrometry data using neural networks, the system including one or more processors and non-transitory computer readable media, the computer implemented system comprising: a mass spectrometer configured to generate a mass spectrometry spectrum data of a peptide (or, in some embodiments, a portion of a peptide or a biological sequence or portion thereof); a processor configured to: generate an input prefix representing a determined amino acid sequence of the peptide. In some embodiments, the determined amino acid sequence of the peptide can include a sequence of one or more amino acids. In some embodiments, the determined amino acid sequence of the peptide can include a "start" symbol and one or more or zero amino acids that have been predicted up to the current iteration. The processor, in these embodiments, is further configured to iteratively update the determined amino acid sequence with a next amino acid. In these embodiments, the computer implemented system comprises a neural network configured to iteratively generate a probability measure for one or more candidate fragment ions (e.g., a candidate fragment ion can be a fragment ion having a particular amino acid at a particular location in the sequence as compared to a separate candidate fragment ion that has a different particular amino acid at that same particular location in the sequence). In some embodiments, there may be a candidate fragment ion each corresponding to each of 20 amino acid residues, their modifications, and special symbols. The iterative generation of a probability measure may be based on one or more fragment ion peaks of the mass spectrometry spectrum data and the corresponding masses of the fragment ion peaks, to determine the next amino acid, wherein the neural network is trained on a known mass spectrometry spectrum data. In some embodiments, the neural network comprises: at least one convolutional layer configured to apply one or more filters to an image data representing the mass spectrometry spectrum data to detect fragment ion peaks; and at least one fully-connected layer configured to determine the presence of a fragment ion peak corresponding to the next amino acid and output the probability measure for each candidate fragment ion.

In some embodiments, the processor is configured to convert the mass spectrometry spectrum data into an intensity vector listing an intensity value for each mass range, and the at least one convolutional layer is configured to apply one or more filters to an image data of the intensity vector. In some embodiments, the intensity value can be a sum of intensity values corresponding to one or more or all fragment ions having a mass in the corresponding range.

In some embodiments, an intensity vector can include or list intensity values for mass ranges or masses. For example, an intensity value can be a sum of one or more intensity values or can be a net intensity value.

In some embodiments, there is provided a computer implemented system for de novo sequencing of peptides from mass spectrometry data using neural networks, the system including one or more processors and non-transitory computer readable media, the computer implemented system comprising a mass spectrometer configured to generate a mass spectrometry spectrum data of a peptide; a processor configured to: convert the mass spectrometry spectrum data into an intensity vector listing intensity values for mass ranges over the mass spectrometry spectrum data, generate an input prefix representing an determined amino acid sequence of the peptide, and iteratively update the determined amino acid sequence with a next amino acid. In these embodiments, the computer implemented system further comprises a neural network configured to iteratively identify the best possible candidate for the next amino acid, wherein the neural network comprises: a convolutional neural network (CNN) configured to generate one or more output vectors representing one or more amino acids represented in the spectrum, using one or more intensity vectors corresponding to image data; and a recurrent neural network (RNN) trained on a database of known peptide sequences, and configured to predict the next amino acid by vector embedding using one or more of the one or more output vectors.

In some embodiments, there is provided a computer implemented system for de novo sequencing of peptides from mass spectrometry data using neural networks, the system including one or more processors and non-transitory computer readable media, the computer implemented system comprising: a mass spectrometer configured to generate a mass spectrometry spectrum data of a peptide; a processor configured to: convert the mass spectrometry spectrum data into an intensity vector listing intensity values for mass ranges over the mass spectrometry spectrum data, generate an input prefix representing an determined amino acid sequence of the peptide, and iteratively update the determined amino acid sequence with a next amino acid. In these embodiments, the computer implemented system further comprises a first neural network configured to iteratively generate a probability measure for all possible candidate fragment ions based on fragment ion peaks of the mass spectrometry spectrum data and the corresponding masses of the fragment ion peaks, to determine the next amino acid, wherein the neural network is trained on a known mass spectrometry spectrum data, and wherein the first neural network comprises: at least one convolutional layer configured to apply one or more filters to an image data representing the mass spectrometry spectrum data to detect fragment ion peaks; and and at least one fully-connected layer configured to determine the presence of a fragment ion peak corresponding to the next amino acid. In these embodiments, the computer implemented system further comprises a second neural network configured to iteratively identify the best possible candidate for the next amino acid, wherein the second neural network comprises: a spectrum-convolutional neural network (spectrum-CNN) configured to encode the mass spectrometry fragment ion data into a feature vector; and a recurrent neural network (RNN) configured to predict a next amino acid in a peptide sequence; wherein the first and second neural networks share at least one common last fully-connected layer configured to output the probability measure for each possible entry for the next amino acid.

Examples

DeepNovo

One embodiment of the system, called DeepNovo is illustrated in FIG. 1. The system takes a spectrum as input and tries to sequence the peptide by predicting one amino acid at each iteration (FIG. 1, see a and b). The sequencing process begins with a special symbol "start". At each sequencing step, the model predicts the next amino acid by conditioning on the input spectrum and on the output of previous steps. The process stops if in the current step the system outputs the special symbol "end". Backward sequencing is performed in a similar way to form the bi-directional sequencing, and the highest-scoring candidate is selected as the final prediction.

Details inside a sequencing step are shown in FIG. 1 (see c). DeepNovo incorporates two classification models that use the output of previous sequencing steps as a prefix to predict the next amino acid. In the first model, the prefix mass is first calculated as the sum of its amino acids' masses and the corresponding terminal. Then, each amino acid type is appended to the prefix and the corresponding theoretical b- and y-fragment ions are identified. For each fragment ion, an intensity window of size 1.0 Dalton around its location on the input spectrum is retrieved. The combined intensity profile of the fragment ions then flows through a convolutional neural network, called ion-CNN.

Ion-CNN

In some embodiments, the ion-CNN is configured to learn features (the peaks) of fragment ions in a spectrum and summarizes the overall information. The input data to the ion-CNN is a prefix, i.e., a sequence including the "start" symbol and the amino acids that have been predicted up to the current iteration. The output is a probability distribution over 20 amino acid residues, their modifications, and three special symbols "start", "end", and "padding". In one embodiment, three modifications are considered: fixed modification carbamidomethylation (C), and variable modifications Oxidation (M) and Deamidation (NQ), hence, a total of 26 symbols are used for prediction. For example, in FIG. 1 (see b and c) where the fourth amino acid is considered, the prefix consists of four symbols "start", "P", "E", "P". Symbol "T" is predicted as the next amino acid ($4^{th}$ amino acid in this example) by sampling or by selecting the highest probability from the model output probability distribution.

Given the input prefix (prefix={start, P, E, P}), in one embodiment, DeepNovo first computes the prefix mass (prefix_mass=mass[N-term]+mass[P]+mass[E]+mass[P]), i.e., the sum of masses of N-terminal and amino acids in the prefix (FIG. 1, see c). Next, DeepNovo tries to add each of 26 symbols to the current prefix and updates its mass accordingly. For each candidate, the corresponding masses of b-ions and y-ions are calculated. In the current implementation, 8 ion types are used: b, y, b(2+), y(2+), b-$H_2O$, y-$H_2O$, b-$NH_3$, and y-$NH_3$ [24] Given an ion mass, DeepNovo identifies its location on the intensity vector using the mass resolution. For example, the prefix of four symbols "start", "P", "E", "P" with the next candidate "T" will have a b-ion of mass 424.2 Da, which corresponds to index 4240 on the intensity vector of resolution 0.1 Da. DeepNovo then extracts an intensity window of size 10 around the ion location. Thus, for each input prefix, DeepNovo computes a 3-dimensional array of shape 26×8×10. Deep learning libraries often process data in batches to take advantage of parallel-computing. Here a batch size of 128 is used, i.e., 128 prefixes were processed at the same time and their arrays are packed into a 4-dimensional array of shape 128×26×8×10. The shape was further transposed into 128× 26×8×10 (explained in further detail below). This final array, denoted by $X^{128\times 26\times 8\times 10}$, is similar to the common data setting of image processing where the 1$^{st}$ dimension is the number of images, the 2$^{nd}$ is the height, the 3$^{rd}$ is the width, and the 4$^{th}$ is the number of channels (e.g., 3 for Red-Green-Blue or 1 for Black-White).

In some embodiments, the ion-CNN model is a convolutional neural network with two convolutional layers and two fully connected layers (FIG. 1, see c) [27,61]. The first convolutional layer uses a 4-dimensional kernel $W^{1\times 3\times 26\times 32}$ and a bias term $B^{32}$ to transform the input array $X^{128\times 26\times 8\times 10}$ into a new array $y^{128\times 8\times 10\times 32}$. This convolution operator slides 26×32=832 receptive fields (filters) of size 1×3 of the kernel W over the input array X and performs a series of dot products and additions as follows:

$$Y_{i,j,k,l} = \sum_{m=1}^{26} \sum_{n=1}^{3} W_{1,n,m,l} X_{i,j,k+n-1,m} + B_l. \quad \text{(Equation 1)}$$

where 1≤i≤128, 1≤j≤8, 1≤k≤10, 1≤l≤32 and the 3$^{rd}$ dimension of X is padded with 0's when needed. The purpose of convolution is to learn as many local features as possible through several different filters. Hence, the kernel W is often called "feature detector" and the output Y is called "feature map". As can be seen from Equation 1, convolution was performed along the 3$^{rd}$ dimension of X, i.e. the intensity window, to learn the bell-shape features, i.e. peaks (FIG. 1, seen c). In some embodiments, different sets of filters were also used for different amino acids. This above is one preferred setting identified after trying multiple convolution combinations of ions and/or amino acids. Other settings or preferred settings are also possible with more data.

In some embodiments, the linear convolution is followed by an activation with Rectified Linear Unit (ReLU), i.e. f(x)=max(0,x). Activation functions are used to add nonlinearity (must have in each layer, add curve) into neural network models and ReLU is preferable because of its many advantages [62]. Thus, the output Z of the first convolutional layer is obtained by applying the ReLU function on Y element-wise:

$$Z_{i,j,k,l} = \text{ReLU}(Y_{i,j,k,l}). \quad \text{(Equation 2)}.$$

The second convolutional layer is applied on top of the first convolutional layer in a similar way with another kernel $V^{1\times 2\times 32\times 32}$. Adding more convolutional layers did not show significant improvement of accuracy, probably because the bell-shape features are not too complicated to learn. In some embodiments, max-pooling is also applied.

In some embodiments, the convolutional layers are followed by a fully-connected layer, or often called hidden layer, of 512 neuron units (FIG. 1, see c). As the name suggests, each unit is connected to every output of the previous convolutional layer to process all local features together. This is done via a linear matrix multiplication and addition as following:

$$Y_{hidden}^{128\times 512} = \text{RELU}(X_{hidden}^{128\times 2,560} W_{hidden}^{2,560\times 512} + B_{hidden}^{512}). \quad \text{(Equation 3)}.$$

The output of the previous convolutional layer with shape 128×8×10×32 is first reshaped into $X_{hidden}^{128\times 2,560}$ to be compatible with the matrix multiplication operator. ReLU is also applied element-wise after the linear operations.

The final fully-connected layer has 26 neuron units, which correspond to 26 symbols to predict. It is connected to the previous hidden layer in a similar way as Equation 3, except that there is no ReLU activation.

In one embodiment, the system also applies dropout; as used herein "dropout" a regularization technique for reducing overfitting in neural networks by preventing complex co-adaptations on training data [63]. It is one way of performing model averaging with neural networks. Dropout was used after the second convolutional layer with probability 0.25 and after the first fully-connected layer with probability 0.5. The idea of dropout is that neuron units are randomly activated (or dropped) at every training iteration so that they do not co-adapt. At the testing phase, all units are activated and their effects are averaged by the dropout probability.

Figure 13:
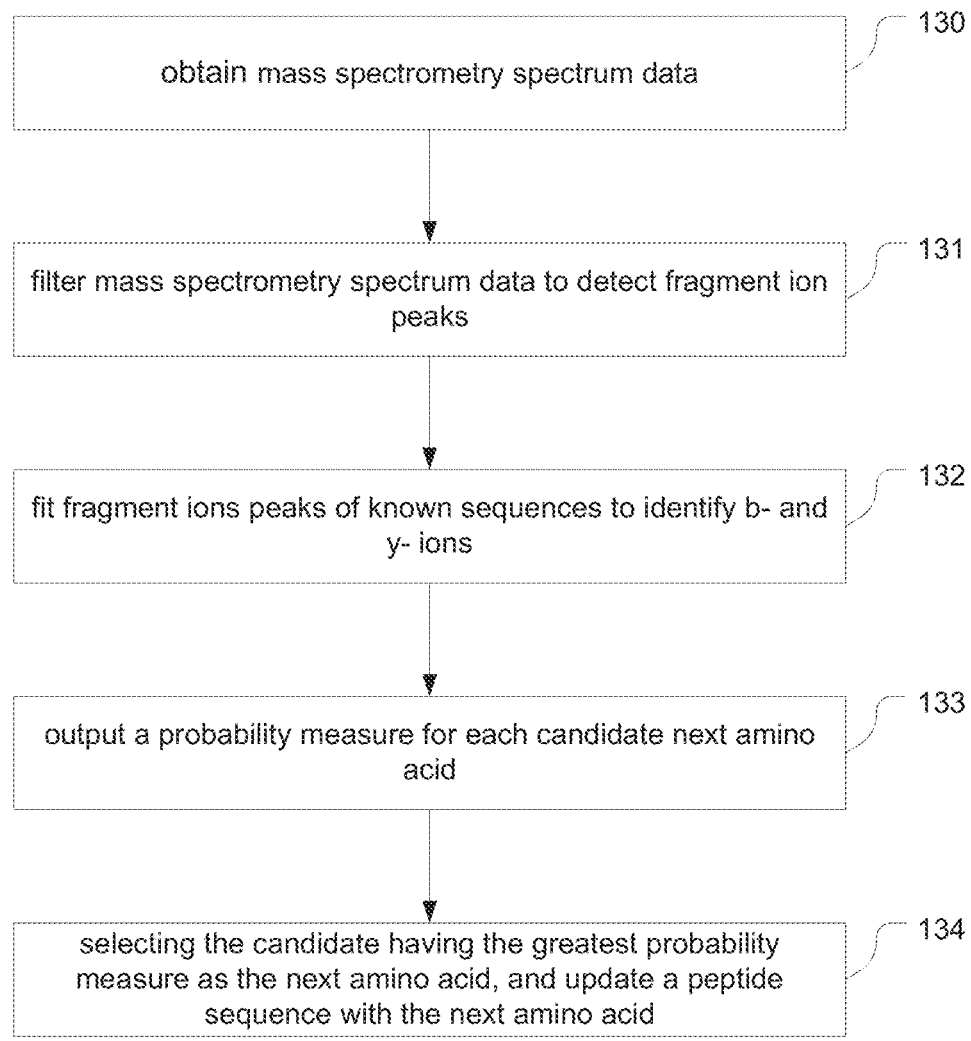
FIG. 13 is a flow chart of an example de novo sequencing procedure using neural networks, by identifying b- and y-ions.

Turning to FIG. 13, one embodiment of a de novo sequencing method is shown, using ion-CNN. A mass spectrometry spectrum data is obtained 130 and inputted into the system comprising a processor and at least one memory providing a plurality of layered nodes configured to form an ion-CNN. Given a staring sequence or given a sequence determined from a previous iteration, the plurality of layered nodes are used to filter the mass spectrometry spectrum data to detect fragment ion peaks in the mass spectrum 131, and then fit fragment ions peaks of known sequences to identify b- and y-ions 133. In some embodiments, the b- and y-ions of the current iteration and those corresponding to the next candidate amino acid in the sequence are identified by fitting. The ion-CNN outputs a probability measure for each candidate next amino acid 133. A candidate having the greatest probability measure is selected as the next amino acid, and peptide sequence is updated accordingly 134. In some embodiments, this method is iterated to determine the full peptide sequence.

Spectrum-CNN and LSTM

Some embodiments of DeepNovo comprises a long short-term memory (LSTM) network, which is one type of recurrent neural networks (RNNs) [34]. The LSTM model represents each amino acid class by an embedding vector, i.e, a collection of parameters that characterize the class (similar to word2vec [37]). Given a prefix, the model looks for the corresponding embedding vectors and sequentially put them through the LSTM network. Moreover, DeepNovo also encodes the input spectrum and uses it to initialize the cell state of the LSTM network [35,36]. For that purpose, the spectrum is discretized into an intensity vector that subsequently flows through another CNN, called spectrum-CNN, before being fed to the LSTM network.

In one embodiment, a spectrum-CNN coupled with LSTM is designed to learn sequence patterns of amino acids of the peptide in association with the corresponding spectrum. In the recently trending topic of "automatically generating a description for an image" referred to above, a convolutional neural network (CNN) is used to encode, or to "understand", the image and a long short-term memory (LSTM) recurrent neural network (RNN) [34] is used to decode, or to "describe", the content of the image [35,36]. DeepNovo considers the spectrum intensity vector as an image (with 1 dimension, 1 channel) and the peptide sequence as a caption. The spectrum-CNN is used to encode the intensity vector and the LSTM to decode the amino acids.

Spectrum-CNN: Simple Version

The input to the spectrum-CNN is, for example, an array of shape 128×1×50,000×1, where 128 is the batch size, 50,000 is the size of intensity vectors given the maximum mass of 5,000 Da (peptide mass) and the resolution of 0.1 Da. As the input size is too large, DeepNovo first tries a simple version of spectrum-CNN that includes two convolutional layers, each with 4 filters of size 1×4, and one fully-connected layer of 512 neuron units. ReLU activation, max-pooling, and dropout are also used in the same way as for the ion-CNN described above.

It should be noted that the pattern recognition problem with tandem mass spectra here is quite different from traditional object recognition problems. Usually an object is recognized by its shape and its features (e.g. face recognition). However, in a tandem mass spectrum, an amino acid is identified by two bell-shape signals, i.e. peaks, whose distance between them has to precisely match with the amino acid mass. Because distance is involved, the simple spectrum-CNN and other common CNN models may not be sufficient.

Spectrum-CNN: Advanced Version

To take the distance into account, in one embodiment the system slices each input intensity vector into pieces based on the amino acid masses. For instance, given that the mass of Alanine, or "A", is 71.0 Da and the resolution is 0.1 Da, we slice the intensity vector from index 710 till the end to create a new vector. The system pads the new vector by 0's so that it has the same size as the original one and concatenate the two along the second dimension to obtain an array of shape 128×2×50,000×1. This procedure is repeated for all 26 symbols and construct a new input array of shape 128×2×50,000×26.

After pre-processing, the system applies the first convolutional layer with kernel of shape 2×10×26×32. The idea is to capture two bell-shape signals in the same filter of size 2×10. This is followed by another convolutional layer with kernel of shape 1×5×32×64 and one fully-connected layer of 512 neuron units. Again, ReLU activation, max-pooling, and dropout are also used. In some embodiments, max-pooling is used aggressively because the intensity vectors are very sparse.

It should be noted that the goal of the spectrum-CNN is not to make accurate prediction of the next amino acid as the ion-CNN. Instead, the spectrum-CNN only tries to pick up signals of which amino acids are presented in the spectrum and provide that information to the LSTM model to better learn sequence patterns of amino acids. In one embodiment, the spectrum-CNN output is a vector of size 512, corresponding to 512 neuron units of its fully-connected layer.

LSTM

Long Short Term Memory (LSTM) networks, one type of Recurrent Neural Networks (RNNs), has one application of which is for the handling of sequential data in Natural Language Processing and Speech Recognition [34]. RNNs are called "recurrent" because they repeat the same computations on every element of a sequence and the next iteration depends on the networks' "memory" of previous steps. For example, one could predict the next word in a sentence given the previous words. In de novo peptide sequencing, embodiments of the system predicts the next amino acid (a symbol), given the previous ones (i.e. the prefix) (see FIG. 1, see b and c), based on the fact that amino acids do not just appear in a random order in protein sequences. Instead, proteins often have particular patterns in their sequences.

In some embodiments, a standard LSTM model is used, detailed of which are known to the skilled person and can be found in literatures such as [34,35,36] or online resources. Configurations of the LSTM used by the present system is described. First, DeepNovo uses embedding vectors of size 512 to represent each of 26 symbols, in a manner similarly to word2vec [37] approach that uses embedding vectors to represent words in a vocabulary. The embedding vectors form a 2-dimensional array Embedding$^{26 \times 512}$. Thus, the input to the LSTM model at each iteration is a vector of size 512. Second, the output of the spectrum-CNN is used to initialize the LSTM model, i.e. being fed as the 0-input. Lastly, the LSTM architecture consists of 1 layer of 512 neuron units and dropout layers with probability 0.5 for input and output. The recurrent iterations of the LSTM model can be summarized as follows:

$$x_0 = \text{CNN}_{spectrum}(I)$$

$$x_{t-1} = \text{Embedding}_{a_{t-1},*}, t>1$$

$$s_t = \text{LSTM}(x_{t-1})$$

where I is the spectrum intensity vector, $a_{(t-1)}$ is the symbol predicted at iteration t−1, Embedding$_{(i,*)}$ is the row i of the embedding array, and $s_t$ is the output of the LSTM and will be used to predict the symbol at iteration t, t=1,2,3, . . . . Similar to the ion-CNN model, the system also adds a fully-connected layer of 26 neuron units to perform a linear transformation of the LSTM 512 output units into signals of 26 symbols to predict.

LSTM networks often iterate from the beginning to the end of a sequence. However, to achieve a general model for diverse species, the present inventors found that it is better to apply LSTM on short k-mers. In some embodiments, further data allows for better optimization for using short k-mers, which the term as used herein refers to smaller units or substrings (k-mer) derived from the peptide in question, the k-mer substring having k-amino acid length.

Figure 14:
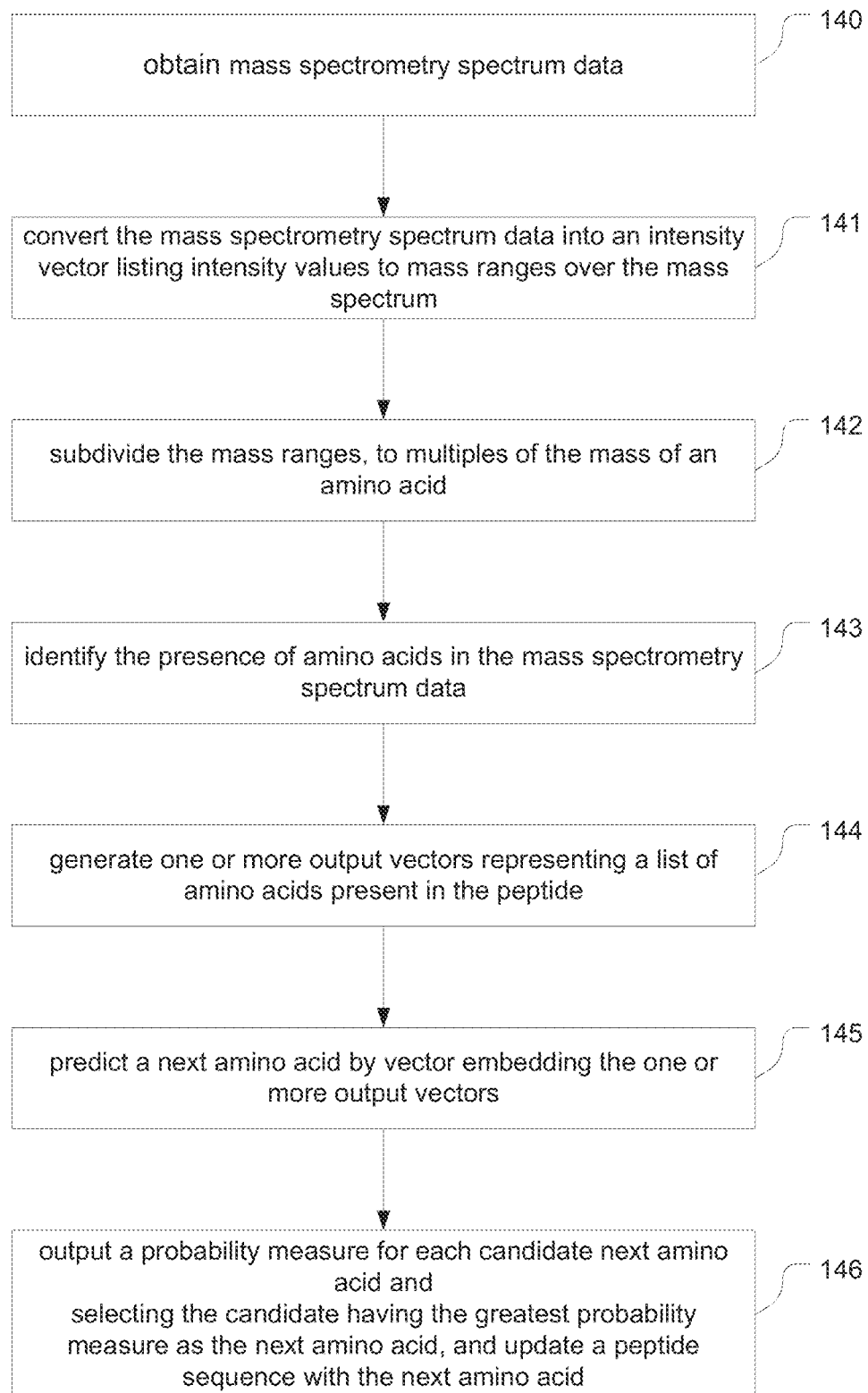
FIG. 14 is a flow chart of an example de novo sequencing procedure using neural networks, by predicting the next amino acid.

Turning to FIG. 14, one embodiment of a de novo sequencing method is shown, using spectrum-CNN and LSTM. A mass spectrometry spectrum data is obtained 140 and inputted into the system comprising a processor and at least one memory providing a plurality of layered nodes configured to form an ion-CNN. Optionally, the mass spectrometry spectrum data is converted into an intensity vector listing intensity values to mass ranges over the mass spectrum 141. Optionally, the intensity vector is sliced by subdividing the mass ranges to multiples of the mass of an amino acid 142. For example, the sliced intensity vector is represented as an array listing intensity values to ranges of masses that are multiples of the mass of an amino acid. The array further lists intensity vectors for each possible amino acid. Given a staring sequence or given a sequence determined from a previous iteration, the plurality of layered nodes are used to identify the next amino acid in the sequence. The presence of amino acids in the mass spectrometry spectrum data is identified 143, and one or more output vectors are generated representing a list of amino acids present in the peptide 144. The next amino acid in the sequence is predicted by vector embedding the one or more output vectors 145. The spectrum-CNN and LSTM output a probability measure for each candidate next amino acid, and a candidate having the greatest probability measure is selected as the next amino acid, and peptide sequence is updated accordingly 146. In some embodiments, this method is iterated to determine the full peptide sequence.

Integrating Ion-CNN and LSTM

In some embodiments that combine the ion-CNN and LSTM, the system first concatenates the outputs of their second-to-last layers, each of size 512, to form a vector of size 1024. Then the system adds a fully-connected layer of 1024 neuron units with ReLU activation, dropout with probability 0.5, and followed by another fully-connected layer of 26 neuron units to perform a linear transformation into signals of 26 symbols to predict (FIG. 1, see c). Thus, the final output of DeepNovo neural networks is a vector of 26 signals, often called logits (unscaled log probabilities). This logits vector will be further used to calculate the loss function during training or to calculate the prediction probabilities during testing.

In some embodiments, all weight and bias parameters, i.e. W's and B's, of the CNNs, embedding vectors, and parameters of the LSTM will be estimated and optimized during the training process. In one embodiment, DeepNovo performs bi-directional sequencing and uses two separate set of parameters, forward and backward, except for the spectrum-CNN and the embedding vectors. The hyper-parameters, such as the numbers of layers, the numbers of neuron units, the size of embedding vector, the dropout probabilities, the number and types of fragment ions, etc. can be configured to define an instance of DeepNovo model.

The outputs of ion-CNN and LSTM are combined to produce a probability distribution over the amino acid classes. The next amino acid can be selected as the one with the highest probability or can be sampled from the distribution. Moreover, given the peptide mass and the prefix mass, DeepNovo calculates the suffix mass and employs knapsack dynamic programming to filter out those amino acids whose masses do not fit the suffix mass. This helps guarantee that final candidate sequences will have the correct peptide mass. Combining all together, DeepNovo then performs beam search, a heuristic search algorithm that explores a fixed number of top candidate sequences at each iteration, until it finds the optimum prediction.

Training Techniques

In one embodiment, the architecture of DeepNovo is shown in FIG. 1.

In some embodiments to train DeepNovo, a dataset is randomly partitioned into three sets: training, validation, and testing. As described herein, due to the one-to-many relationship between peptide and spectra, it is important to make sure that the three sets do not share peptides to avoid over-fitting. The training dataset is processed in mini-batches. At each training step, a mini-batch is randomly selected from the training dataset and fed to the model. The model is provided with a real prefix and is asked to predict the next amino acid. The output logits and the real amino acid are then used to calculate the cross-entropy loss function. Next, back-propagation is performed to calculate gradients (partial derivatives) and update the parameters using the Adam optimizer [49]. During the training, loss function was periodically calculated the on the validation set and decide to save the model if there is an improvement.

Training DeepNovo with MS/MS Data

Example, methods for training DeepNovo is described. First, MS/MS data has a special property: the same peptide could appear multiple times in a dataset with different spectra. Such spectra may have different fragment ions, and even if they share some major ions, the intensities of those ions also vary from spectrum to spectrum. However, the system is able to learn some common features of different spectra that come from the same peptide, and those features are not generalized well to other peptides. This problem will lead to over-fitting if a dataset is randomly partitioned into training, validation, and testing sets (a common technique in most model training tasks). The system will perform well on those three sets, but its performance worsens on a new dataset. To avoid or minimize over-fitting, in some embodiments, the training, validation, and testing sets are partitioned such that they do not share common peptides. In preferred embodiments, more data from a wide variety of sources are collected rather than increasing data from the same source.

GPUs and Big Data: Two Advantages of Neural Network Models

Current developments in neural networks and deep learning are driven by the two main engines: powerful CPUs and massive amount of datasets. De novo peptide sequencing is a computation-intensive optimization problem and modern mass spectrometry instruments often produce data faster than many sequencing softwares can analyze in real time. Novor is one example known sequencing software, however it still lacks precisions. In one preferred embodiment, the system comprises high-performance hardware such as CPUs instead of traditional CPUs. In some embodiments, DeepNovo is implemented on the Google TensorFlow™ platform and is able to run on both CPUs and CPUs. Moreover, TensorFlow scales up easily to multiple CPUs, CPUs, and even different workstations, maximizing most computational resources.

In one embodiment study, 50 thousands spectra from each dataset were used for training, i.e. about 10% of the total data for training (for testing, all data were used). In some embodiments, additional spectra many be used for training, for example, 20% of the total data, 30% of the total data, 40% of the total data, or 50% or more of the total data. In embodiments where 10% of the total data were used for training corresponding to 50 thousands spectra from each dataset, the accuracy of DeepNovo was already 7.7-22.9% higher than existing systems and methods. In some embodiments, increasing the amount of training data also increases system accuracy. In some embodiments, neural network models such as DeepNovo are preferable and benefits the most from large proteomics databases such as PRIDE™, MassIVE™, and other publically available databases known to a skilled person.

Datasets and Benchmark Criteria

The performance of DeepNovo in comparison with existing de novo peptide sequencing tools including PEAKS (version 8.0, [38]), Novor [19], and PepNovo [12] were evaluated. Two sets of data were used for performance evaluation: lowresolution and high-resolution, from previous publications. The low-resolution set includes seven datasets [39-45] (see Table 1). The first five datasets were acquired from Thermo Scientific LTQ Orbitrap™ with the Collision-Induced Dissociation (CID) technique. The other two were acquired from Thermo Scientific Orbitrap Fusion™ with the Higher-energy Collisional Dissociation (HCD) technique. The high-resolution set includes nine datasets acquired from Thermo Scientific Q-Exactive™ with the HCD technique [52-60] (see Table 2). Data from a wide variety of species and research groups were chosen to ensure an unbiased evaluation. All datasets can be downloaded from the ProteomeXchange™ database and the Chorus database. Details about the datasets and LC-MS/MS experiments are found in Tables 1 and 2.

TABLE 1

Summary of the seven low-resolution datasets. PSMs: Peptide Spectrum Matches; FDR: False Discovery Rate.

| | | Total | | Error Tolerance | | |
|---|---|---|---|---|---|---|
| Species | Number of RAW files | Number of Spectra | Number of PSMs (1% FDR) | Precursor Mass (ppm) | Fragment Ion (da) | Accession Number |
| M. musculus | 40 | 792,148 | 355,514 | 10 | 0.6 | PXD002247 |
| C. elegans | 108 | 1,125,050 | 437,097 | 20 | 0.8 | PXD000636 |
| E. coli | 70 | 3,239,116 | 1,174,817 | 20 | 0.5 | PXD002912 |
| D. melanogaster | 18 | 681,968 | 178,853 | 20 | 0.5 | PXD004120 |
| H. sapiens | 27 | 804,473 | 497,191 | 10 | 0.6 | PXD002179 |
| S. cerevisiae | 6 | 558,564 | 280,377 | 20 | 0.5 | The link is available in reference [44] |
| P/aeruginosa | 25 | 2,781,682 | 603,601 | 20 | 0.3 | PXD004560 |

SUPPLEMENTARY TABLE 2.

Summary of the nine high-resolution datasets. PSMs: Peptide Spectrum Matches; FDR: False Discovery Rate.

| | | Total | Number of | Error Tolerance | | |
|---|---|---|---|---|---|---|
| Species | Number of RAW files | Number of Spectra | PSMs (1% FDR) | Precursor Mass (ppm) | Fragment Ion (da) | Accession Number |
| V. mungo | 19 | 735,618 | 37,775 | 20 | 0.05 | PXD005025 |
| M. musculus | 9 | 276,648 | 37,021 | 10 | 0.05 | PXD004948 |
| M. mazei | 16 | 800,768 | 164,421 | 10 | 0.05 | PXD004325 |
| Bacillus | 14 | 571,615 | 291,783 | 30 | 0.05 | PXD004565 |
| C. endoloripes | 9 | 1,862,619 | 150,611 | 20 | 0.05 | PXD004536 |
| S. lycopersicum | 60 | 603,506 | 290,050 | 15 | 0.05 | PXD004947 |
| S. cerevisiae | 5 | 277,077 | 111,312 | 20 | 0.05 | PXD003868 |
| A. mellisfera | 17 | 822,069 | 314,571 | 20 | 0.05 | PXD004467 |
| H. sapiens | 26 | 684,821 | 130,583 | 20 | 0.02 | PXD004424 |

PEAKS DB software (version 8.0, [38]) was used with a false discovery rate (FDR) of 1% to search those datasets against the UniProt database and the taxon of the sample. The peptide sequences identified from the database search were assigned to the corresponding MS/MS spectra and were then used as groundtruth for testing the accuracy of de novo sequencing results. Supplementary Tables S1 and S2 show the summary of PEAKS DB search results for the low-resolution and high-resolution datasets, respectively.

Leave-one-out cross validations were performed. In each validation, all except one of the datasets were used for training DeepNovo (from scratch) and the remaining dataset was used for testing. Other tools are previously trained by their authors and were only tested on all datasets. The training datasets and the testing dataset come from different species. Cross validation was performed to guarantee unbiased training and testing and does not give DeepNovo any advantage. All tools were configured with the same settings including fixed modification Carbamidomethylation (C), variable modifications Oxidation (M) and Deamidation (NQ), fragment ion and precursor mass error tolerances (see Supplementary Tables S1, S2).

To measure the accuracy of de novo sequencing results, the real peptide sequence and the de novo peptide sequence of each spectrum were compared. A de novo amino acid is considered "matched" with a real amino acid if their masses are different by less than 0.1 Dalton and the prefix masses before them are different by less than 0.5 Dalton. Such an approximate match is used instead of an exact match because of the resolution of the benchmark datasets. The total recall (and precision) of de novo sequencing was calculated as the ratio of the total number of "matched" amino acids over the total length of real peptide sequences (and predicted peptide sequences, respectively) in the testing dataset. The recall was also calculated at the peptide level, i.e. the fraction of real peptide sequences that were fully correctly predicted. All sequencing tools report confidence scores for their predictions. The confidence scores reflect the quality of predicted amino acids and are valuable for downstream analysis (e.g. reconstructing the entire protein sequence from its peptides [21]). Setting a higher threshold of confidence scores will output a smaller set of peptides with high precision, but leaving the rest of the dataset without results, and hence, leading to lower recall; and vice versa. Hence, given the availability of recall, precision, and confidence scores, precision-recall curves are drawn and the area under the curves (AUC) is used as a summary of de novo sequencing accuracy [47]. These measures of sequencing accuracy are known and described, for example, in the following publications [10, 12, 19] the contents of which are incorporated herein by reference.

Comparison of De Novo Sequencing Accuracy

Figure 2:
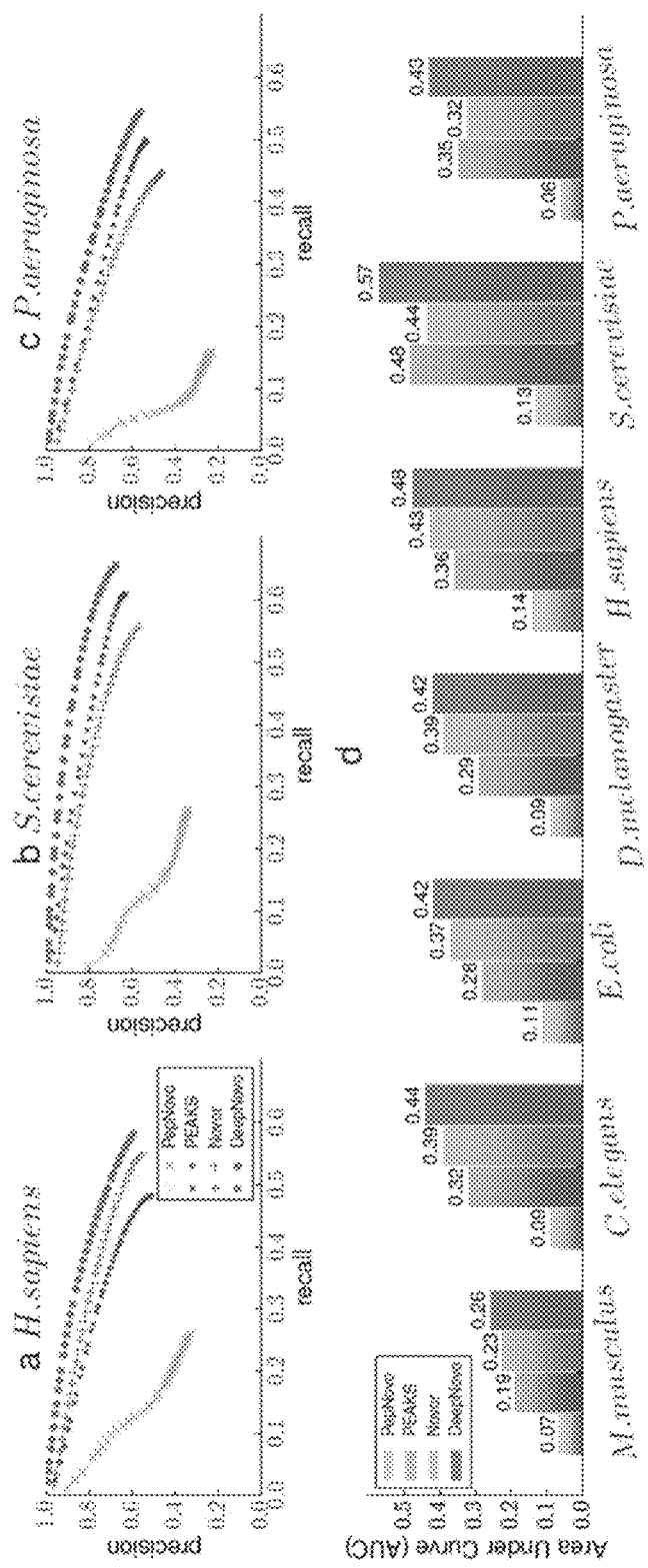
FIG. 2 shows the precision-recall curves and the area under the curves(AUC) of 695 PepNovo, PEAKS, Novor and DeepNovo. a. Precision-recall curves on 696 H.sapiens. b. Precision-recall curves on S.cerevisiae. c. Precision-recall curves 697 on P.aeruginosa. d. AUC of the four sequencing tools on seven datasets.
Figure 6:
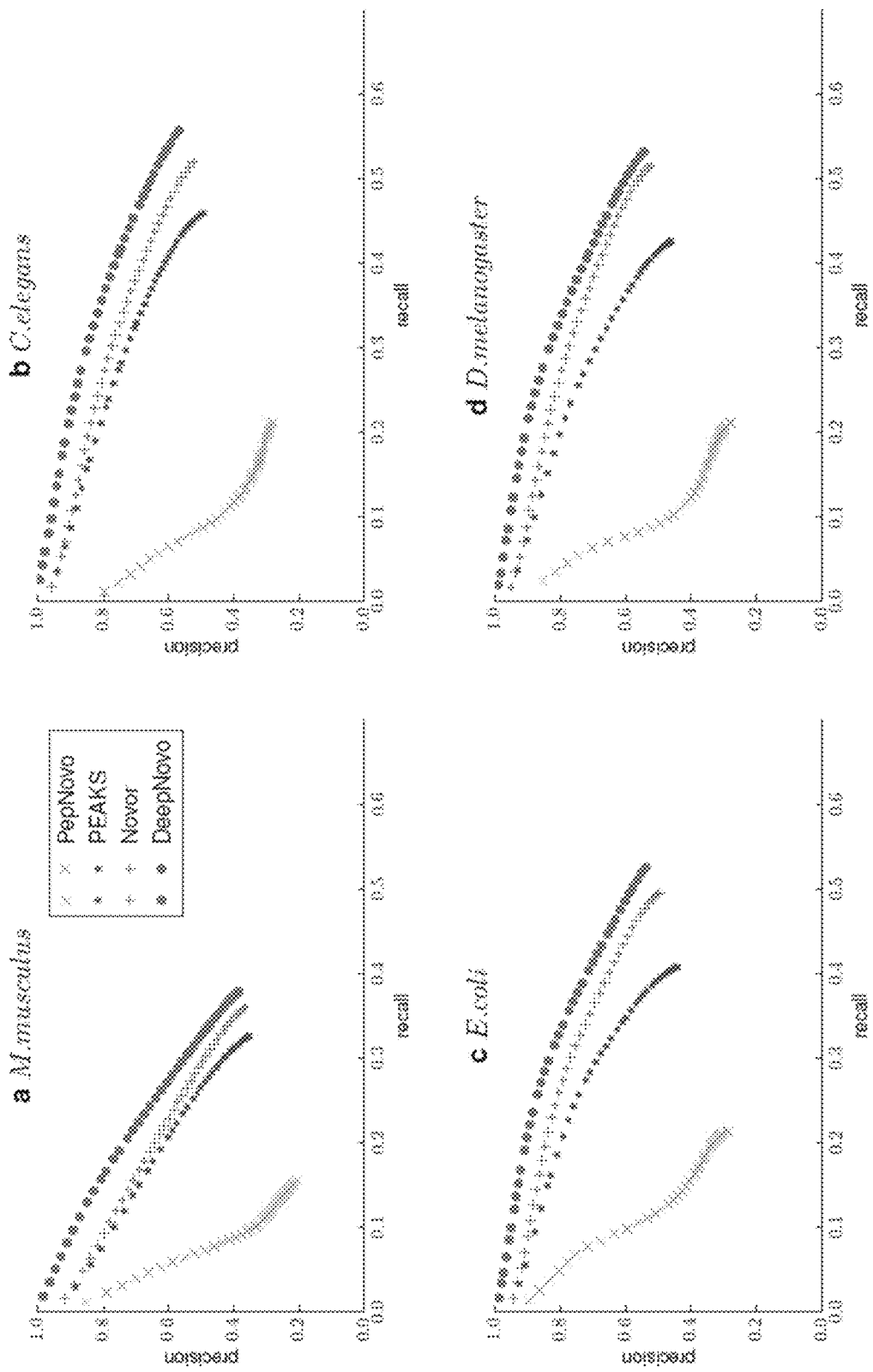
FIG. 6 shows the precision-recall curves of the de novo sequencing results on other four low-resolution datasets. a. The precision-recall curves on M.musculus. b. The precision-recall curves on C.elegans. c. The precision-recall curves on E.coli. d. The precision-recall curves on D.melanogaster.
Figure 7A:
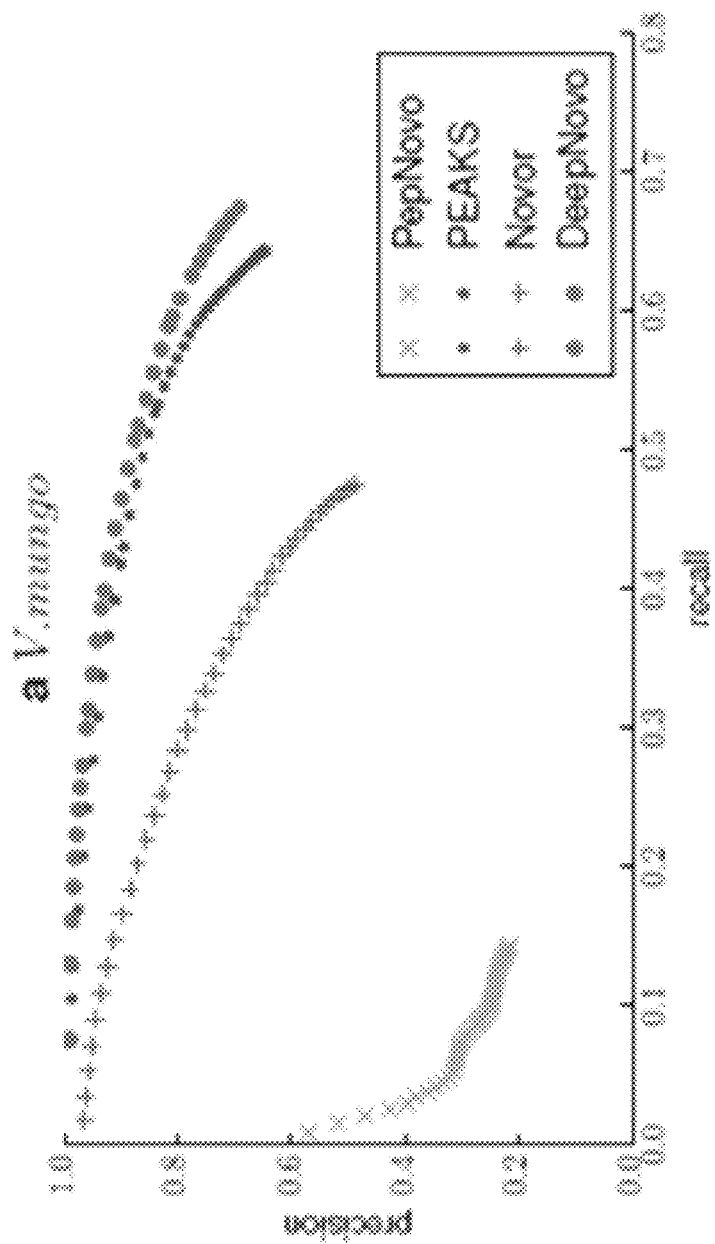
FIGS. 7A, 7B, 7C, 7D, 7E, 7F, 7G, 7H, and 7I show the precision-recall curves of PepNovo, Novor, PEAKS and DeepNovo on nine high-resolution datasets.
Figure 7B:
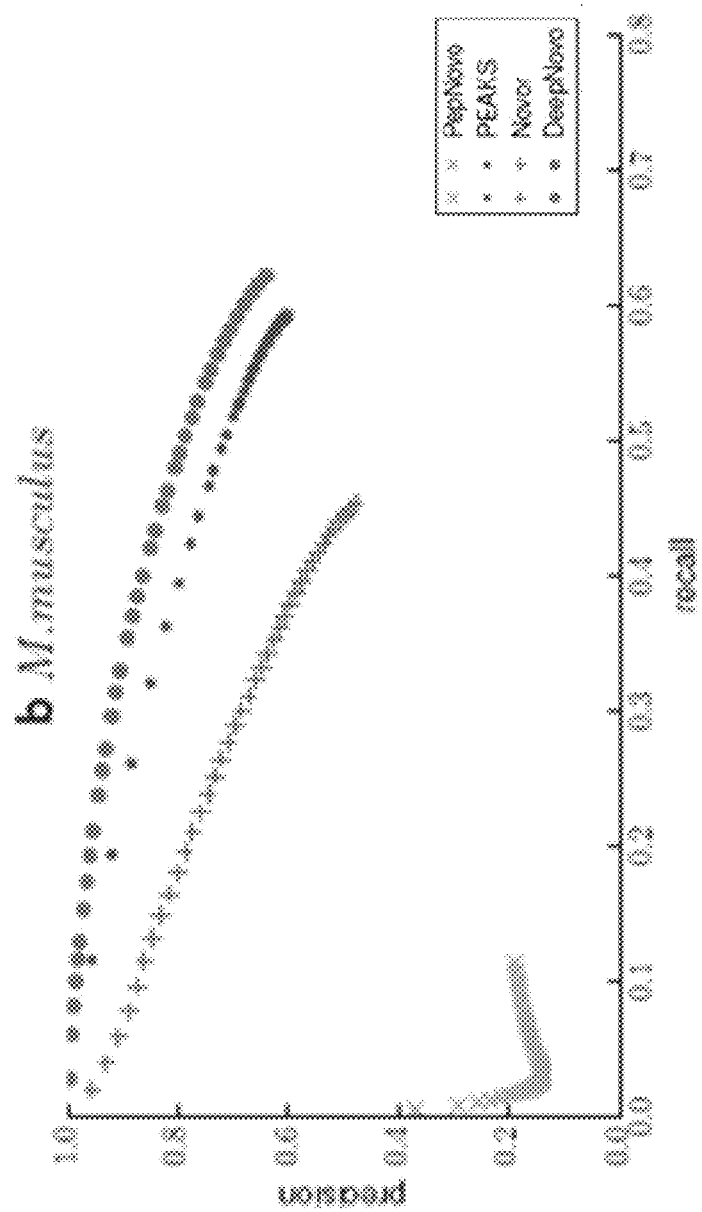
Figure 7C:
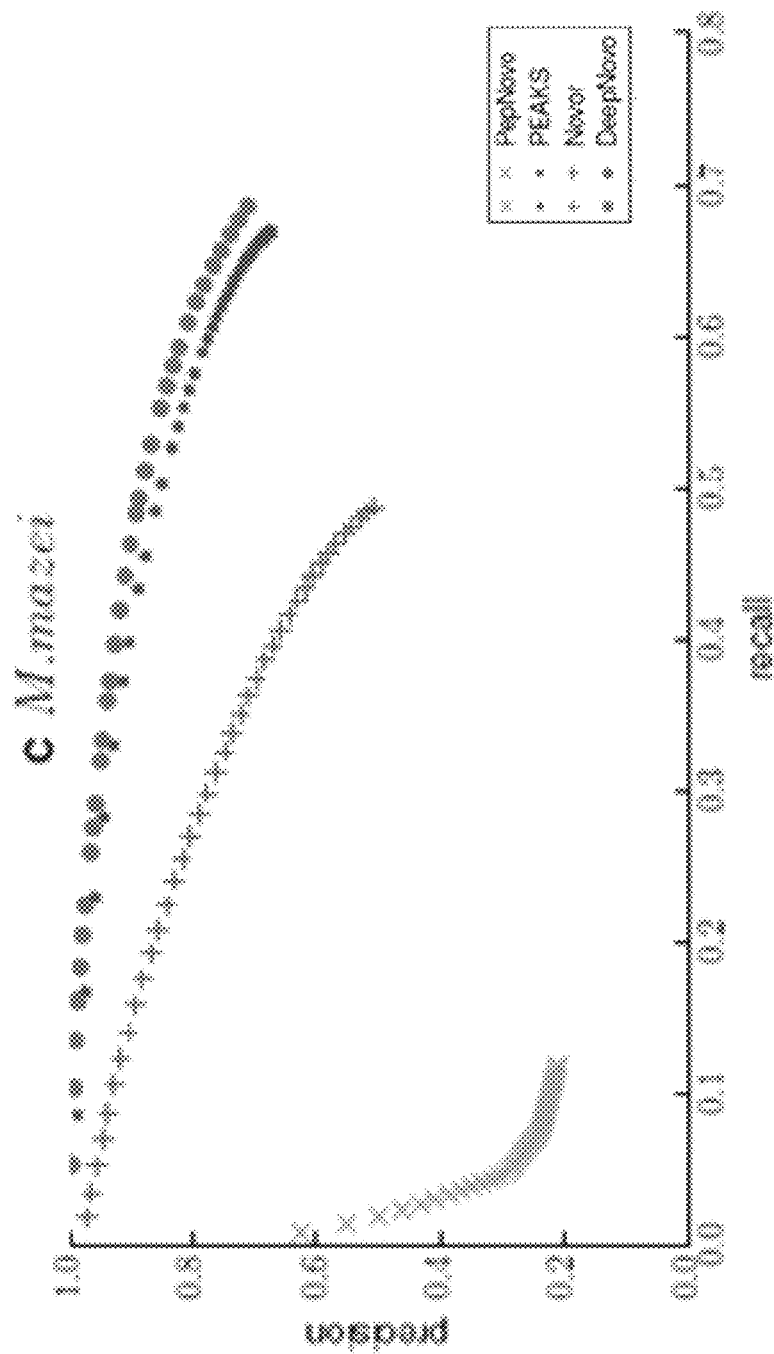
Figure 7D:
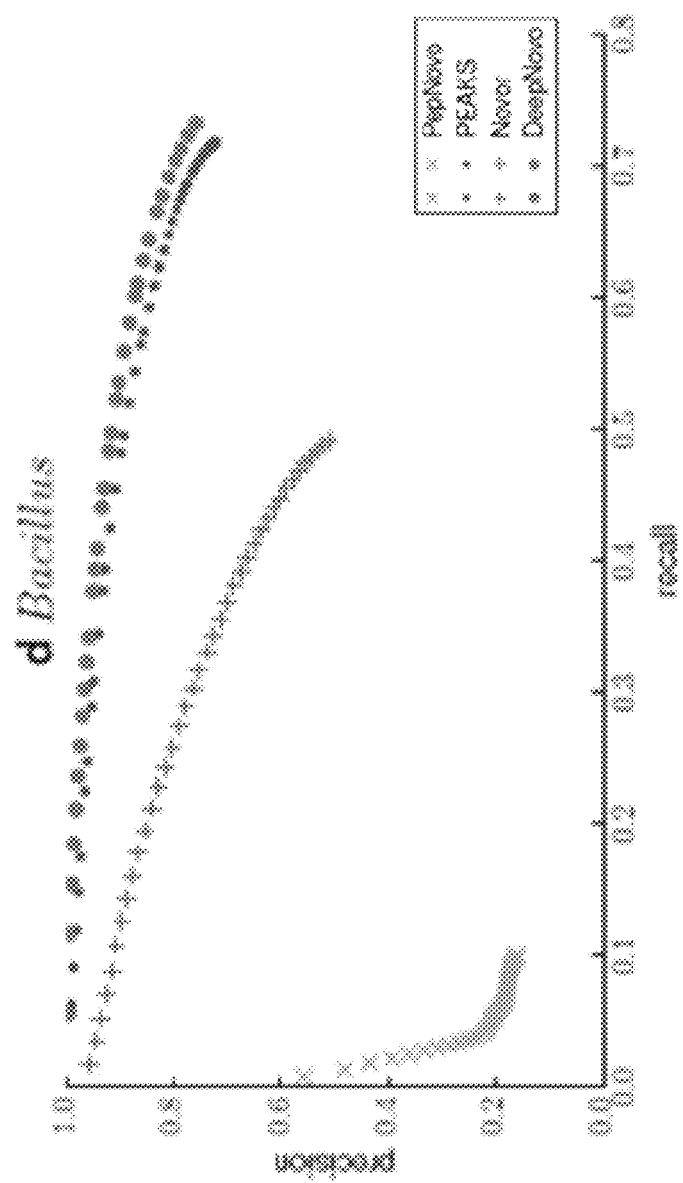
Figure 7E:
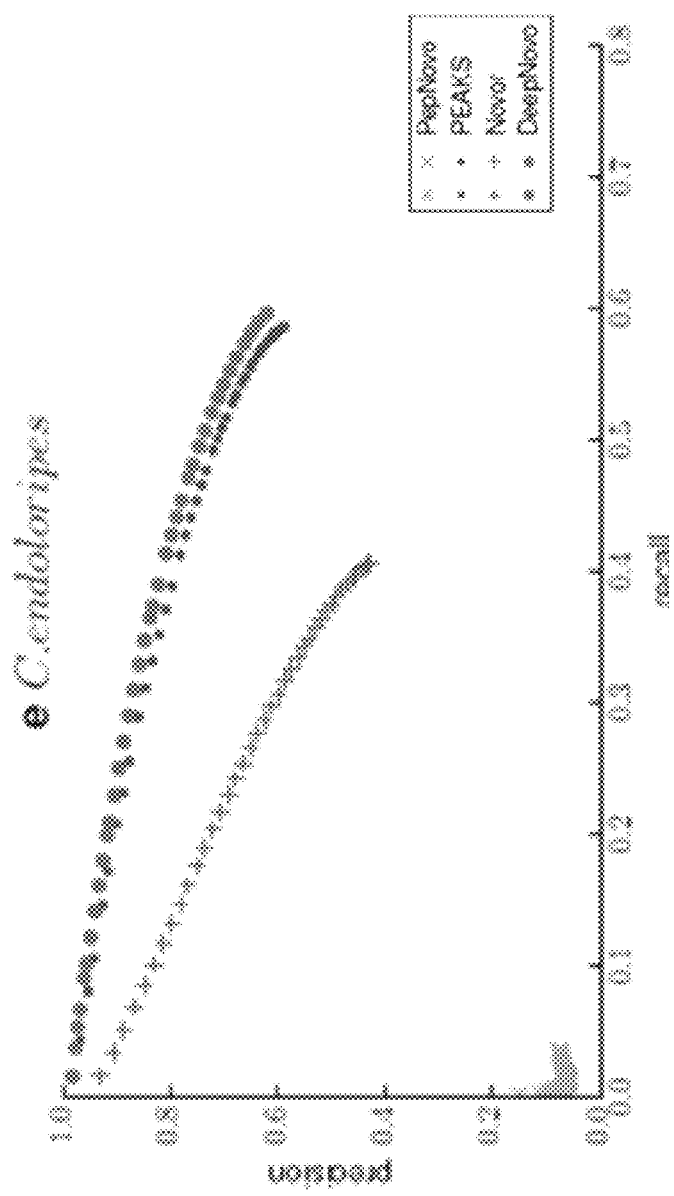
Figure 7F:
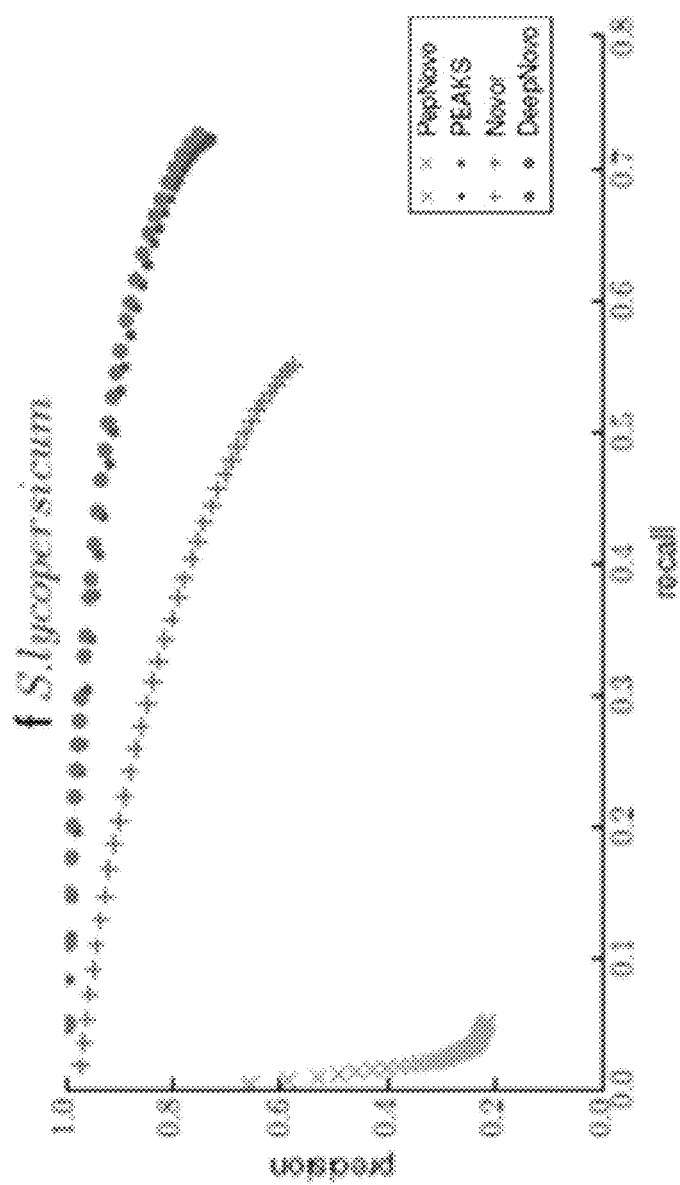
Figure 7G:
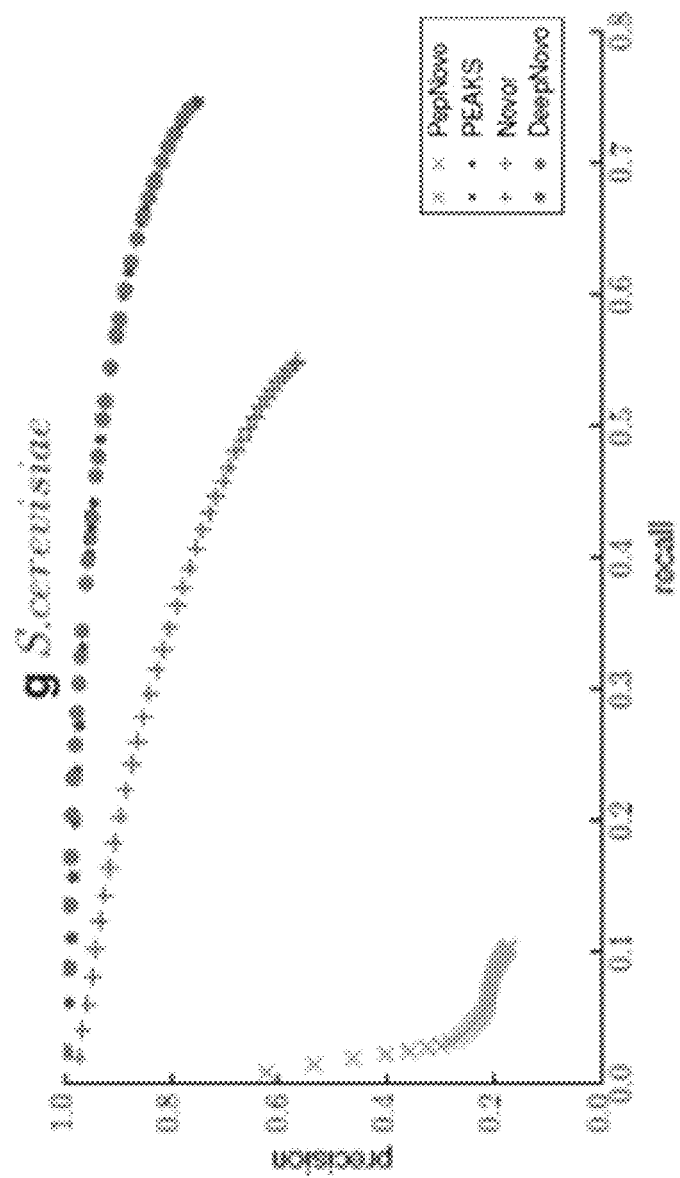
Figure 7H:
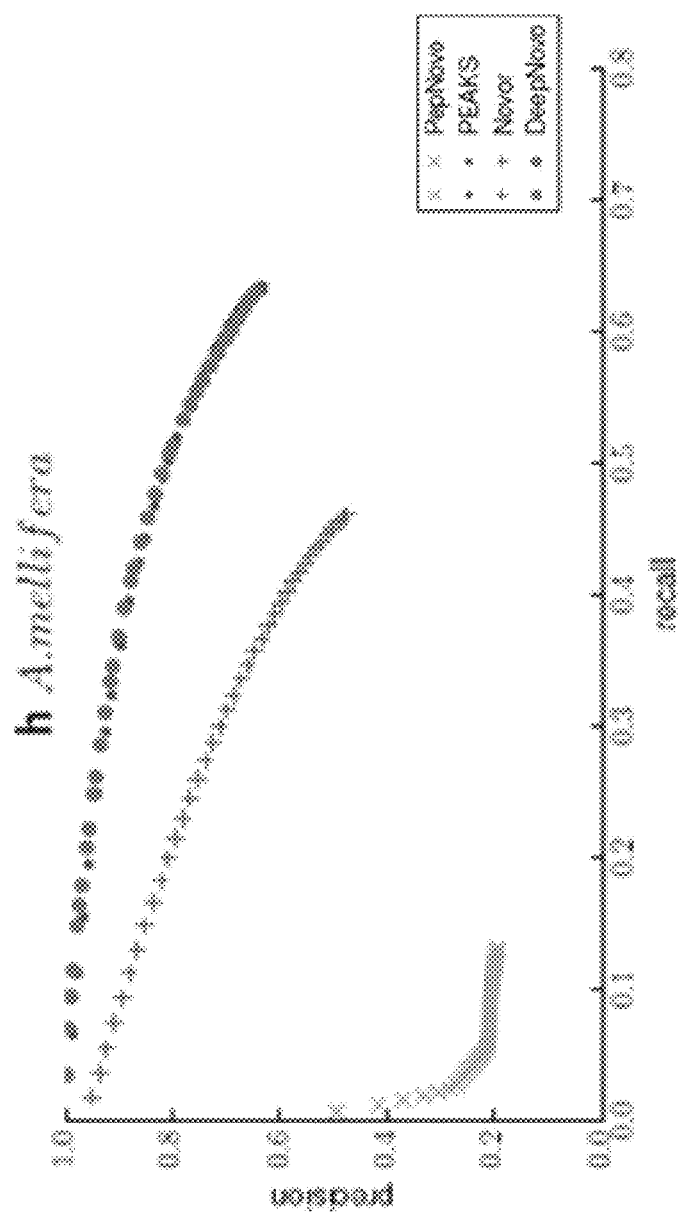
Figure 7I:
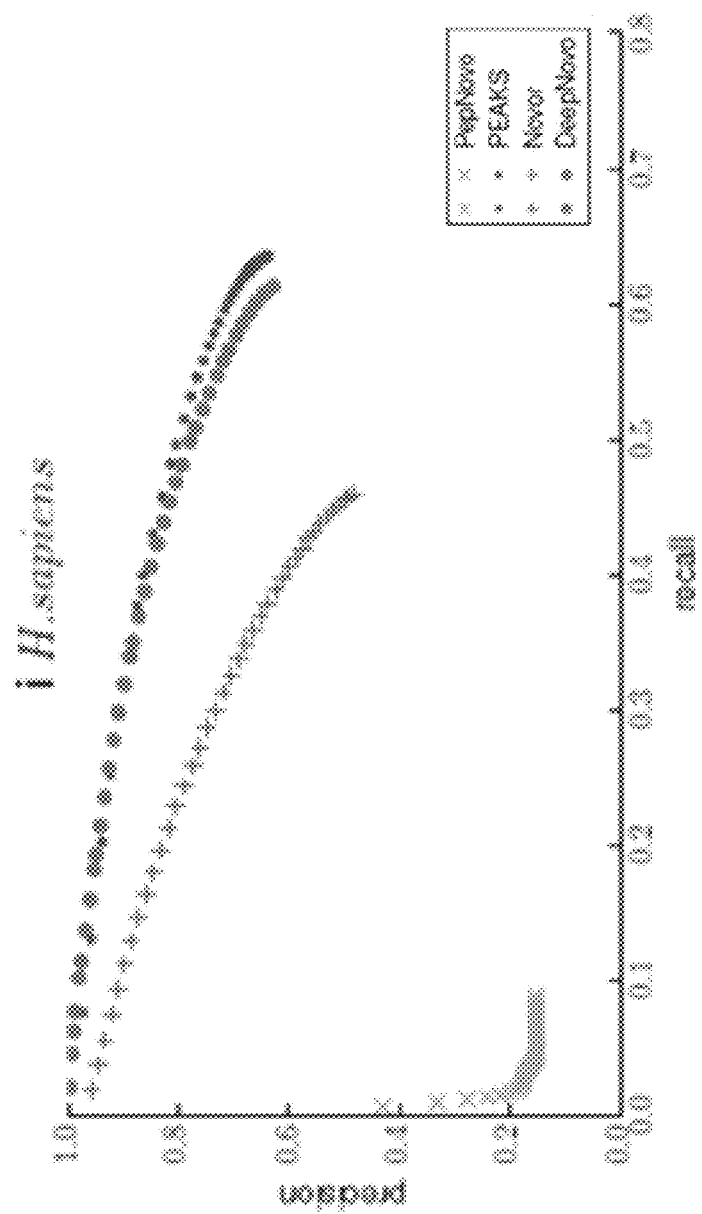
Figure 7J:
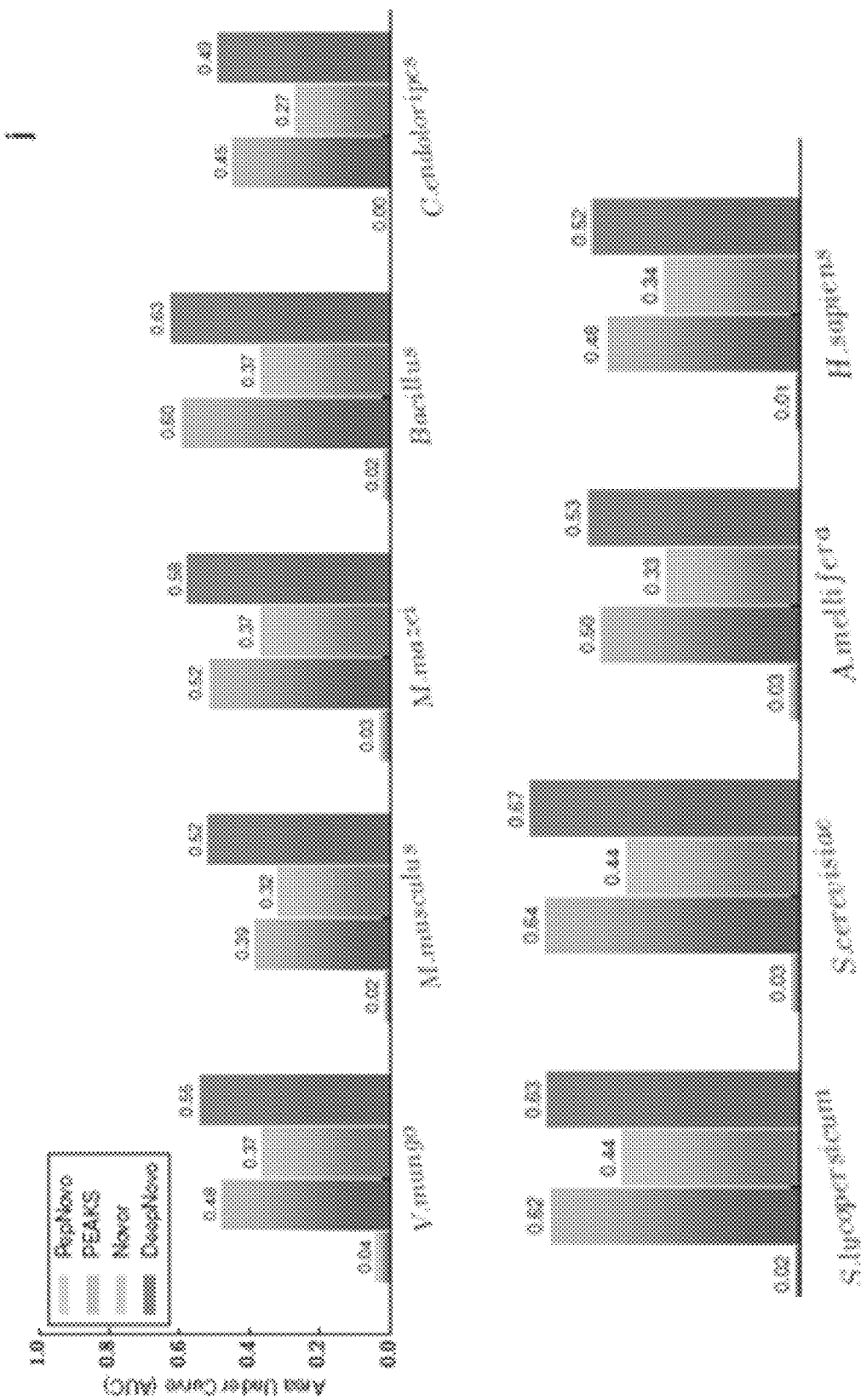
FIG. 7J shows area under the curves (AUC) of PepNovo, Novor, PEAKS and DeepNovo on the nine datasets.

FIG. 2 and FIG. 6 show the precision-recall curves and the AUC of de novo sequencing tools on the seven lowresolution datasets. DeepNovo outperformed other tools across all seven datasets. In particular, for *Homo sapiens*, the AUC of DeepNovo was 33.3% higher than that of PEAKS (0.48/0.36=1.333) and 11.6% higher than that of Novor (0.48/0.43=1.116). PEAKS and Novor often came in the second place while PepNovo fell behind. Novor performed relatively better on CID data while PEAKS performed relatively better on HCD data. The AUC of DeepNovo was 18.8-50.0% higher than PEAKS, 7.7-34.4% higher than Novor, and overall, 7.7-22.9% higher than the second best tool across all seven datasets. The improvement of Deep-Novo over existing methods was better on HCD data than on CID data, probably because the HCD technique produces better fragmentations and hence more patterns for Deep-Novo to learn. The evaluation results described herein demonstrates the improved accuracy of the present systems and methods over existing sequencing tools on a wide variety of species.

Figure 3:
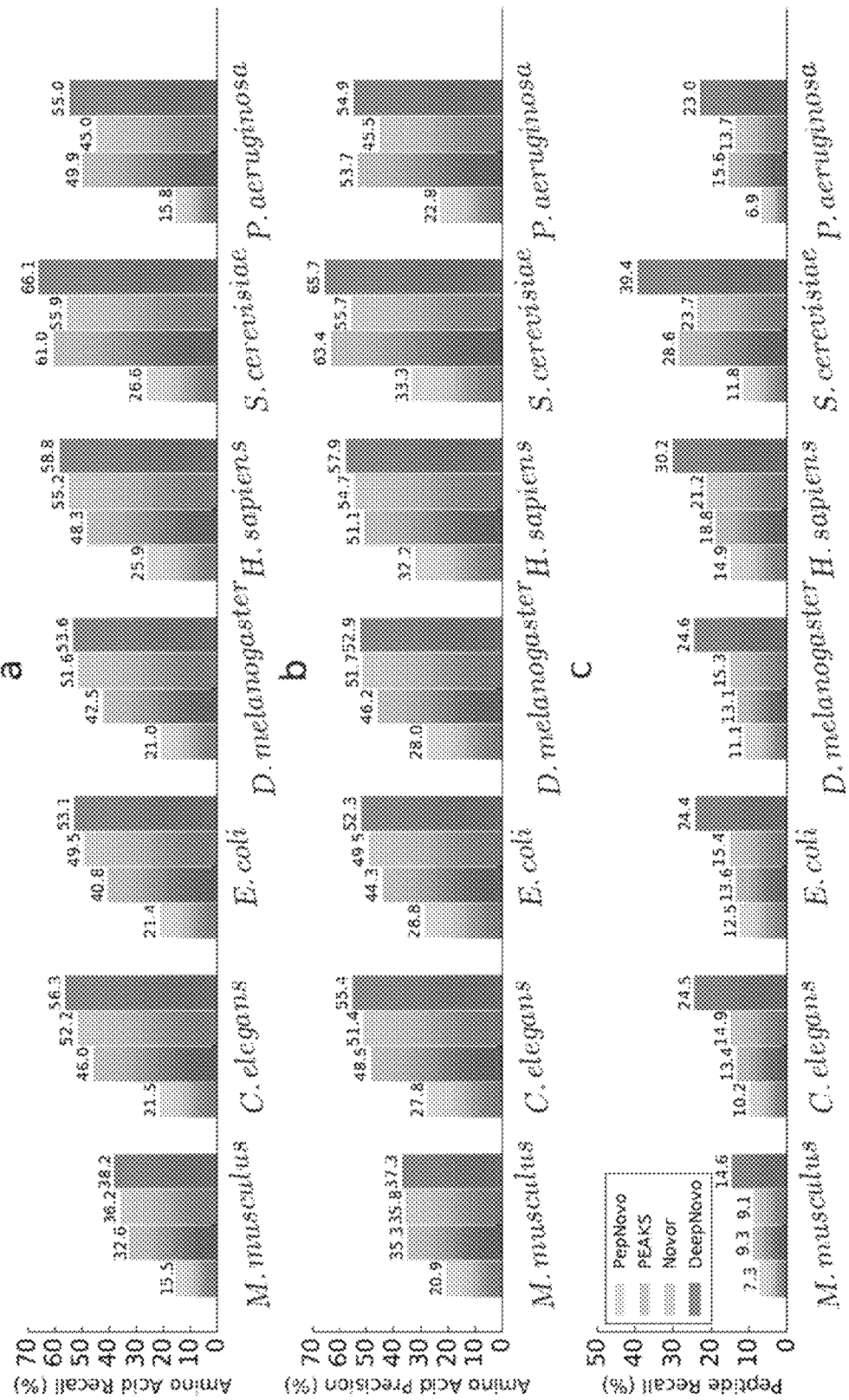
FIG. 3 shows the total recall and precision of PepNovo, PEAKS, Novor and DeepNovo on seven datasets. a. Recall at amino acid level. b. Precision at amino acid level. c. Recall at peptide level.

FIG. 3 (see a and b) show the total recall and precision, respectively, of de novo sequencing results on the seven datasets. Here all sequencing results were used from each tool, regardless of their confidence scores. DeepNovo achieved both higher recall and precision than other tools. DeepNovo recall was 8.4-30.2% higher than PEAKS and 3.9-22.1% higher than Novor. DeepNovo precision was 2.3-18.1% higher than PEAKS and 2.4-20.9% higher than Novor.

FIG. 3 (see c) shows the total recall of de novo sequencing tools at the peptide level. MS/MS spectra often have missing fragment ions, making it difficult to predict a few amino acids, especially those at the beginning or the end of a peptide sequence. Hence, de novo sequenced peptides are often not fully correct. Those few amino acids may not increase the amino acid-level accuracy much but they can result in substantially more fully-correct peptides. As shown in FIG. 3 (see c), DeepNovo showed better performance than existing sequencing tools; DeepNovo's recall at the peptide level was 38.1-88.0% higher than PEAKS and 42.7-67.6% higher than Novor. This demonstrates the advantage of the LSTM model in DeepNovo that makes use of sequence patterns to overcome the limitation of MS/MS missing data.

Figure 8A:
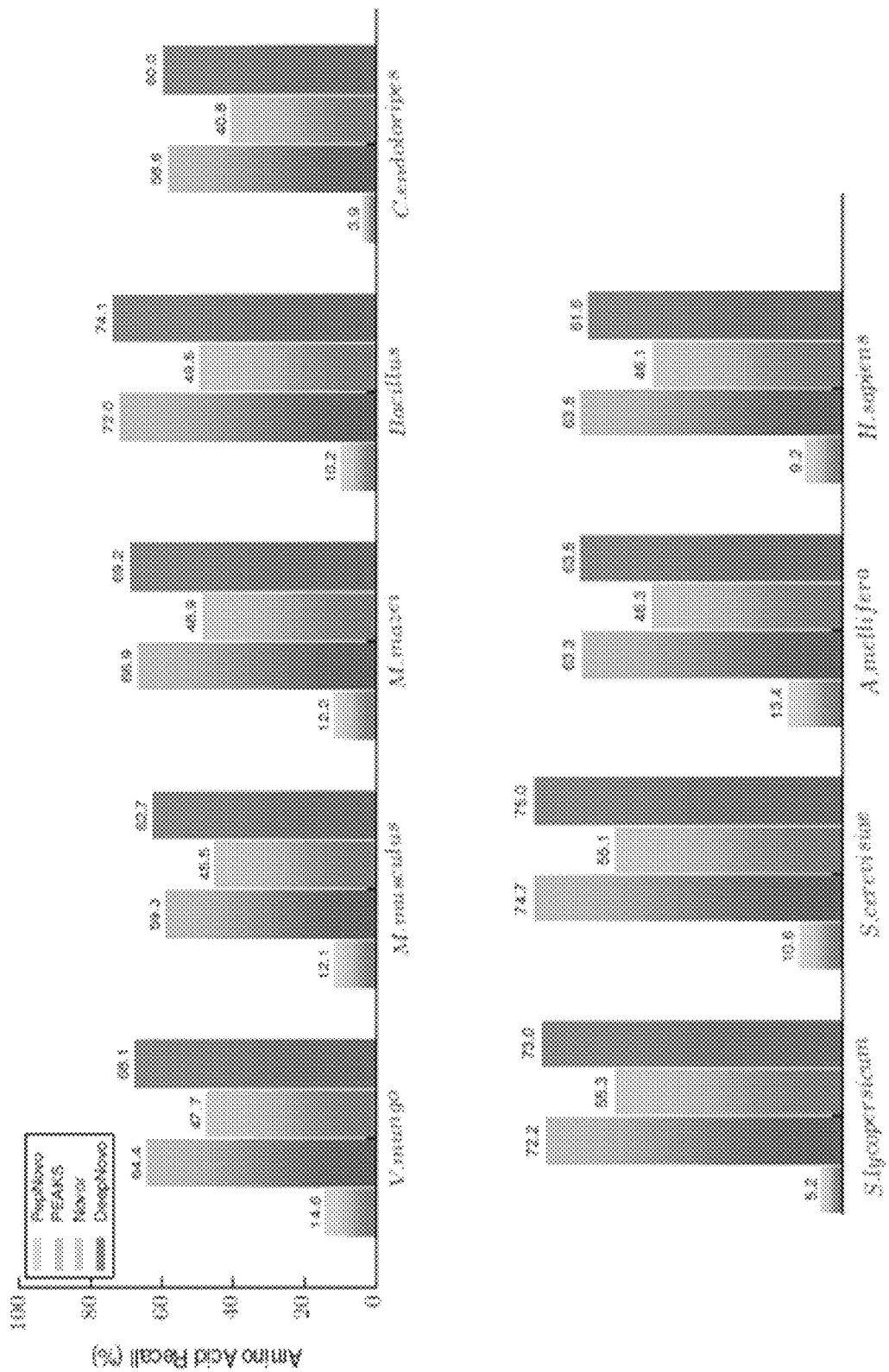
FIGS. 8A, 8B, and 8C show the total recall and precision of PepNovo, Novor, PEAKS and DeepNovo on nine high-resolution datasets.
Figure 8B:
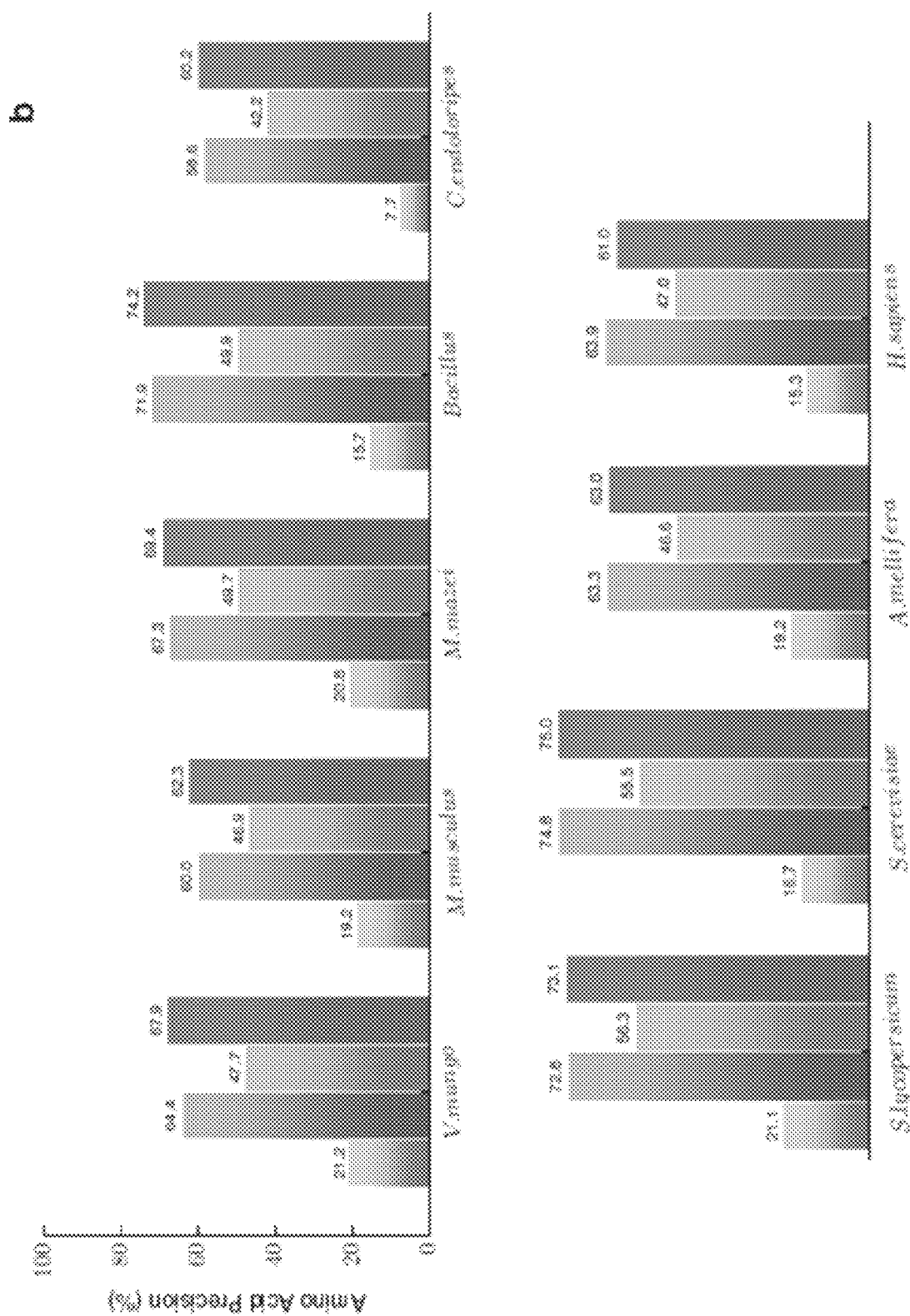
Figure 8C:
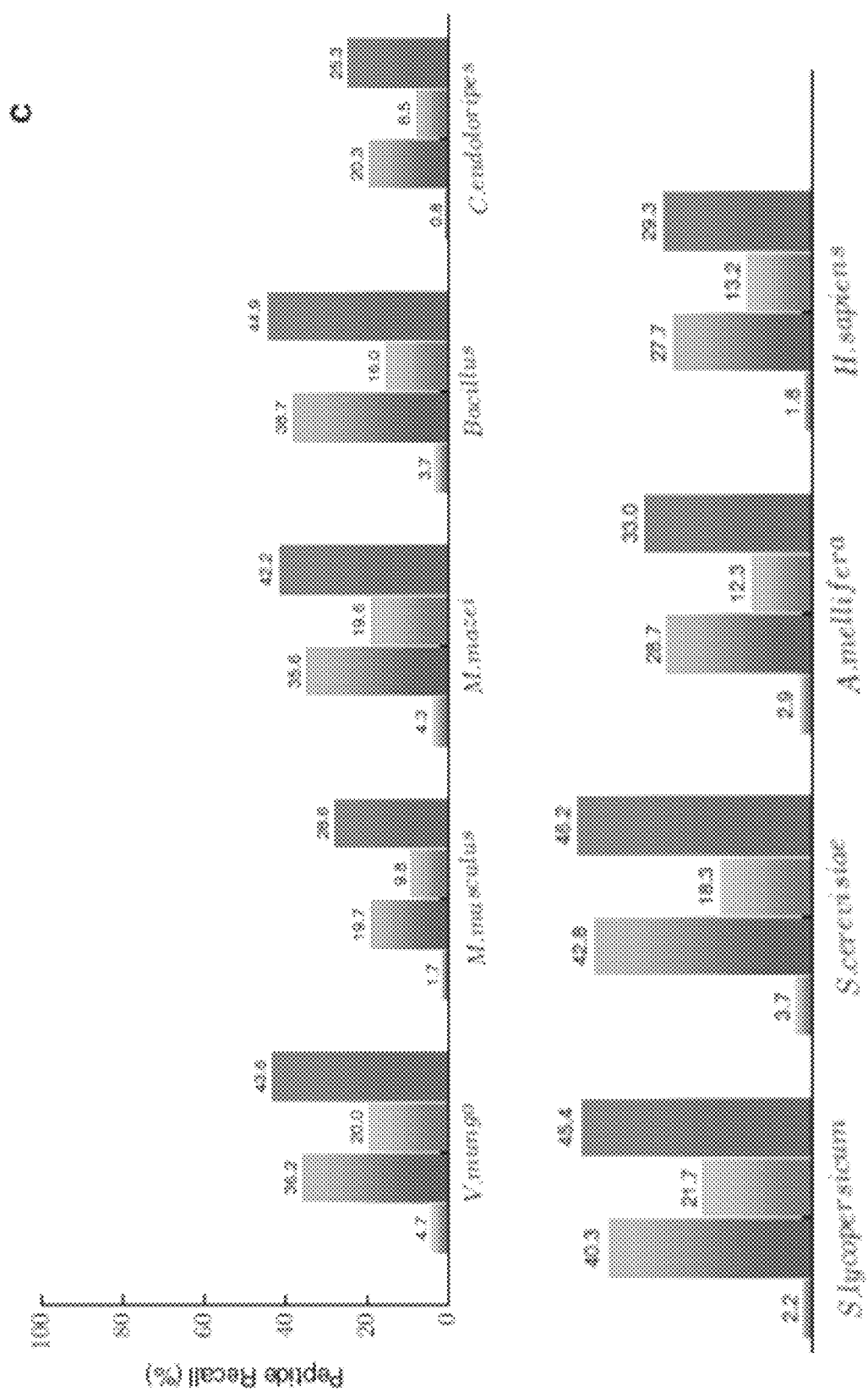

FIGS. 7A to 7J show the evaluation results on the nine high-resolution datasets. Novor and PepNovo were not trained with this type of data and hence their performance was not as good as PEAKS and DeepNovo. As can be seen from FIG. 7J, the AUC of DeepNovo performed better than that of PEAKS across all nine datasets by 1.6-33.3%. FIGS. 8A to 8B show that the total amino acid recall of DeepNovo was 0.2-5.7% higher than that of PEAKS for eight datasets, and 3.1% lower than PEAKS for the *Homo Sapiens* dataset. At the peptide level, the total recall of DeepNovo was 5.9-45.6% higher than PEAKS across all nine datasets.

Figure 11:
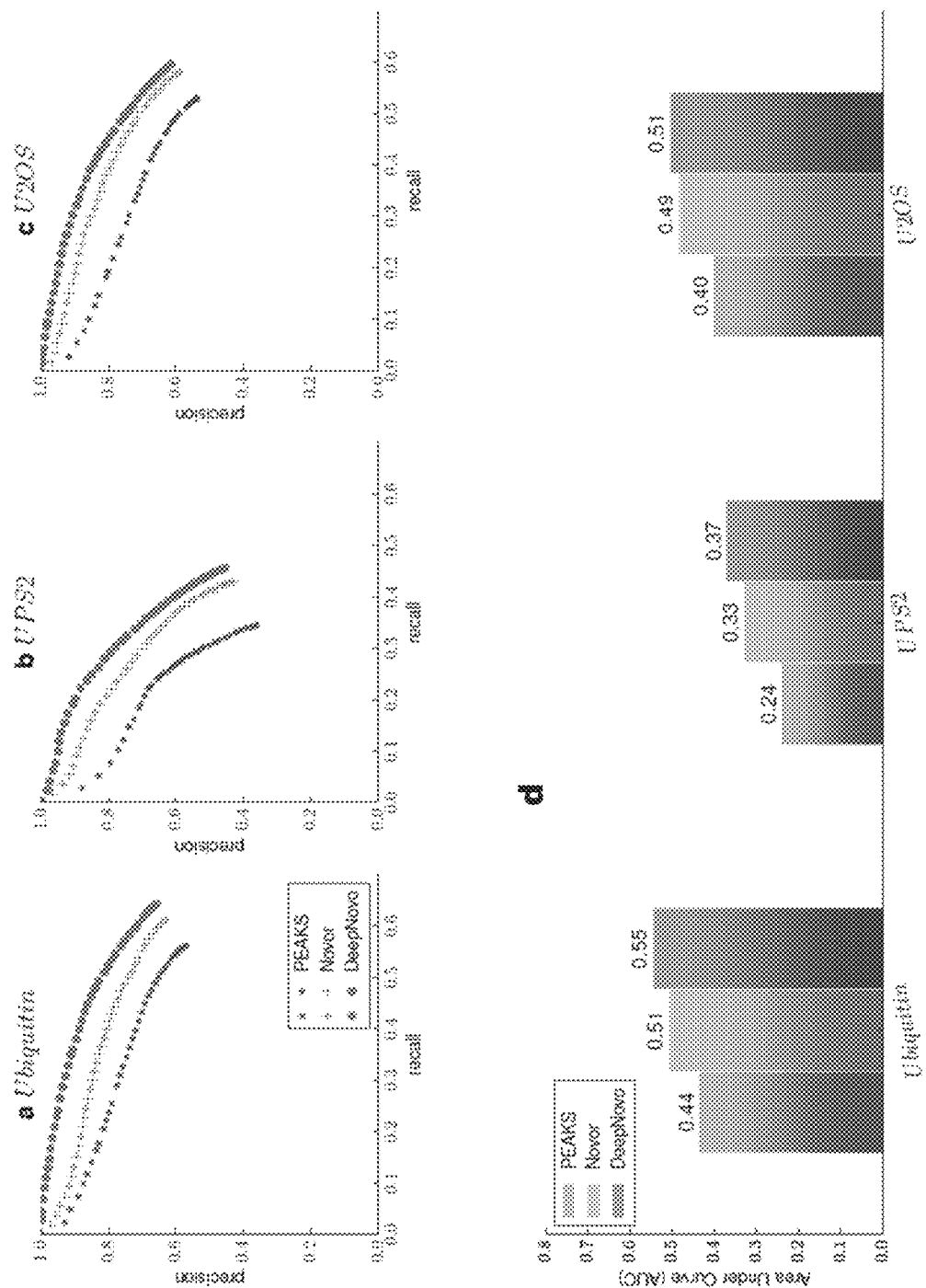
FIG. 11 shows the precision-recall curves and the area under the curves (AUC) of PEAKS, Novor and DeepNovo on three public real datasets. a. Precision-recall curves on Ubiquitin. b. Precision-recall curves on UPS2. c. Precision-recall curves on U2OS. d. AUC of the three sequencing tools on the three real datasets.

DeepNovo, Novor, and PEAKS were also evaluated on three testing datasets identified in the Novor paper [19]. The results were consistent with those described above and DeepNovo achieved 4.1-12.1% higher accuracy than the other existing tools (FIG. 11).

De novo Peptides Identified by DeepNovo but Missed by Database Search

In some instances, DeepNovo found high quality matches that eluded database search identification. To show this, an experiment on a conventional data set "Clinical Proteomic Tumor Analysis Consortium" (CPTAC) was performed as follows.

Figure 12:
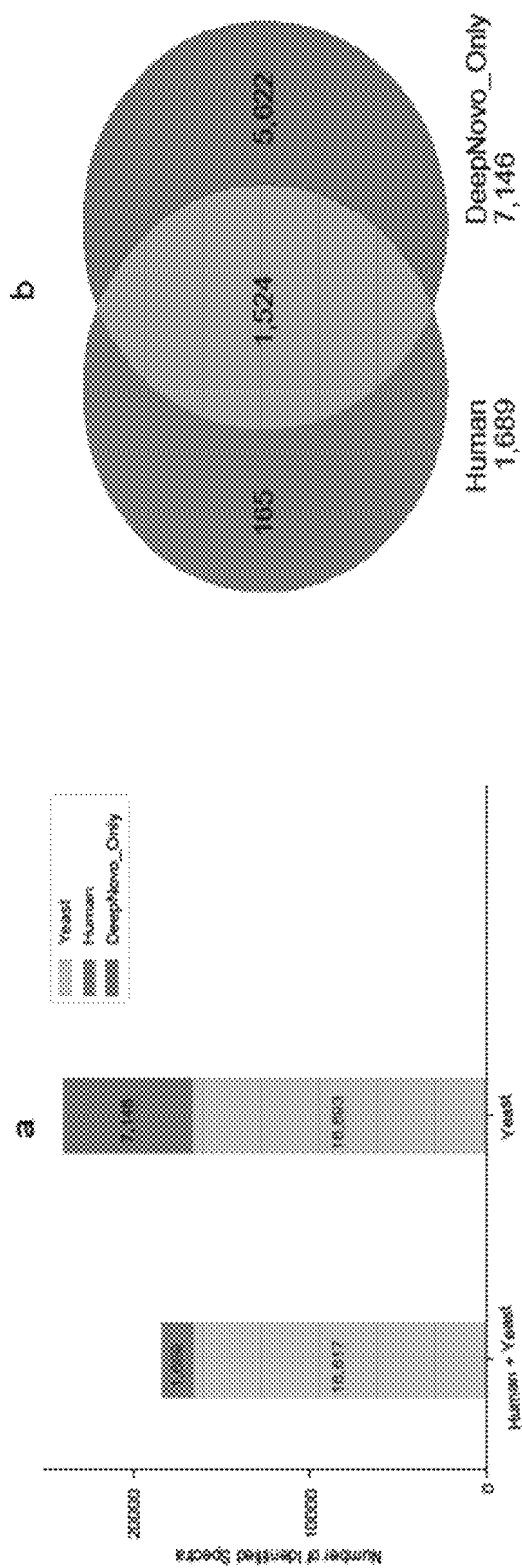
FIG. 12 shows the identification of spectra with de novo high scores and yet elude database search. a. The number of spectra identified by searching human-yeast database, yeast database only, and using DeepNovo. b. The Venn diagram of spectra matched with human peptides and DeepNovo only.

A yeast lysate was spiked with a mixture of 48 human proteins (Sigma-Aldrich UPS1). The sample was then ana-lyzed three times by Thermo LTQ-Orbitrap instrument. PEAKS DB was then used to perform database search with a false discovery rate (FDR) of 1%. This dataset was first searched against a combined database including both human and yeast proteins. As shown in FIG. 12 (see a), the total number of identified peptide-spectrum matches (PSMs) is 18,306, including 16,617 from yeast and 1,689 from human. Next, this dataset was searched against the yeast database only and found 16,693 PSMs.

DeepNovo was used to perform de novo sequencing on the whole dataset. After excluding 16,693 spectra identified from the yeast database search and selecting the top 50% high-confidence results, 7,146 spectra was identified by DeepNovo only. Among those 7,146 spectra, 1,524 matched to the human peptides identified in the first round of database search and covered ~93% (1,524/1,631) of total human PSMs (FIG. 11 (see b)). Thus, DeepNovo was able to identify human peptides that eluded the second round of database search. This demonstrates the importance of de novo sequencing when the database information is missing.

Performance of Neural Networks Models in DeepNovo

Figure 4:
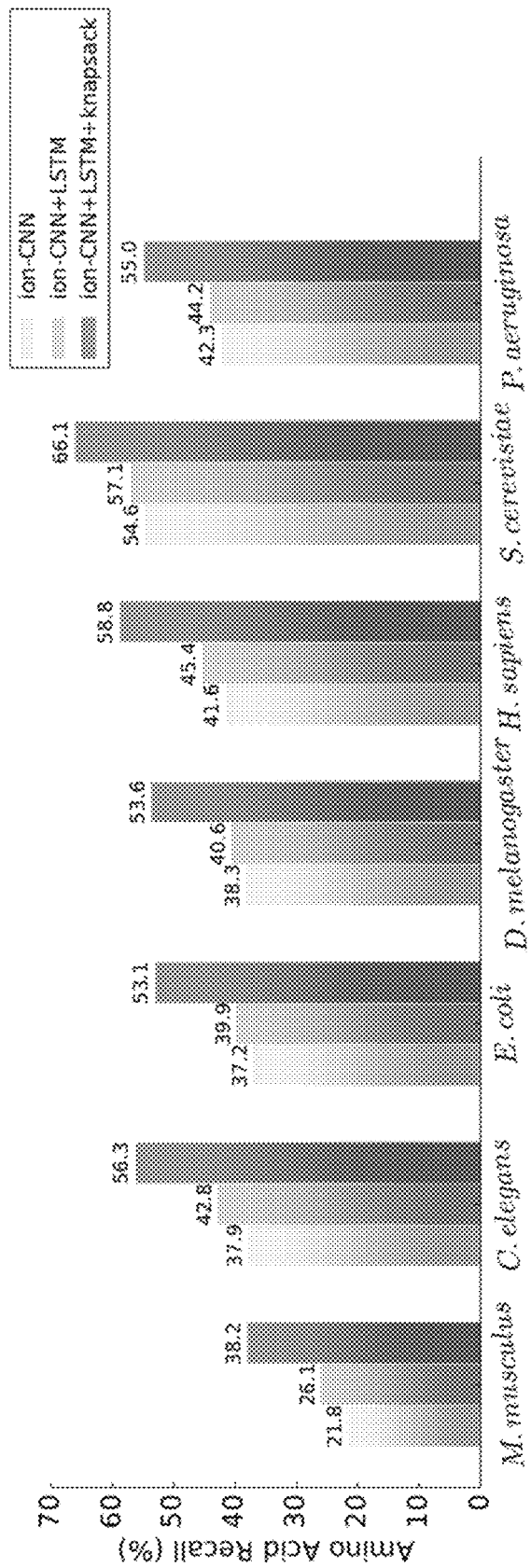
FIG. 4 shows the contributions of DeepNovo's components to its total recall on seven datasets.

In some embodiment, the improvement of DeepNovo over existing sequencing systems and methods comes from its two classification models, ion-CNN and LSTM, combined with knapsack dynamic programming. FIG. 4 shows a detailed breakdown of how those components contributed to the total recall. In some embodiments, the system uses ion-CNN and LSTM individually or collectively. In some embodiments, the neural networks are trained together, while in other embodiments they are trained separately and combined via the last hidden layer. While it is not a simple cumulative increasing of accuracy when one combines multiple models, further improvements to one of the models may also improve the overall accuracy of the system.

Reconstructing Antibody Sequences with DeepNovo

Figure 9:
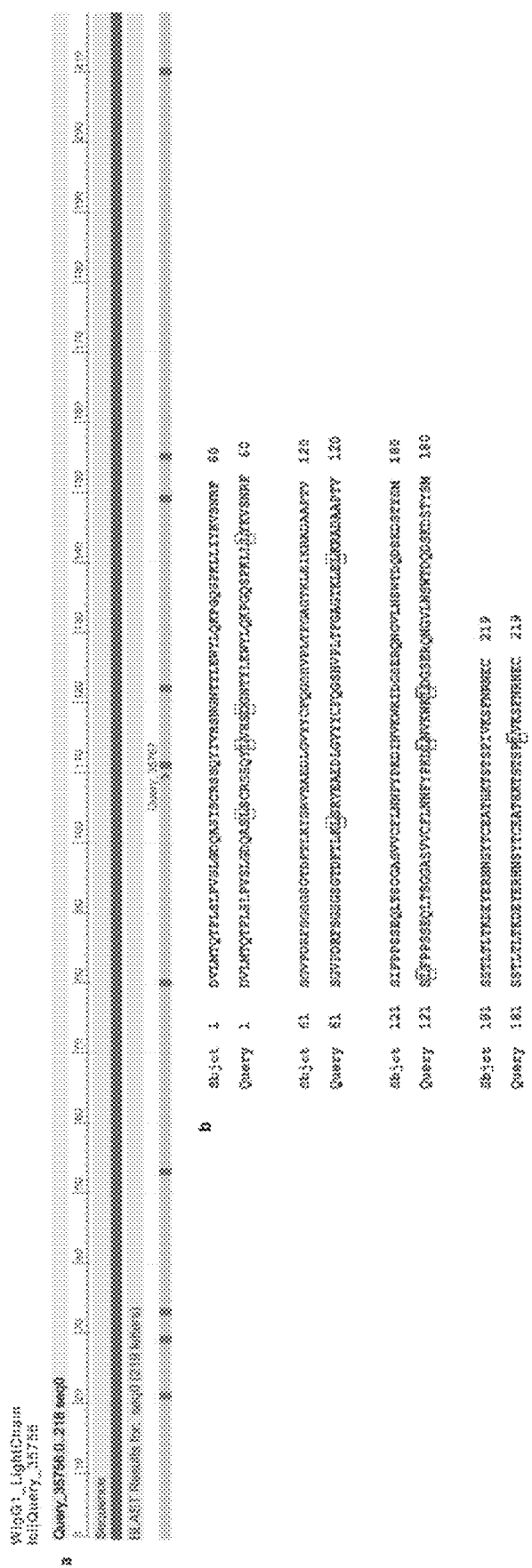
FIG. 9 shows Deepnovo assembly result for the WIgG1 light chain. "Sbjct" is listed as SEQ ID No:1; "Query" is listed as SEQ IS No:2. a. BLAST alignment of the full-length assembled contig against the target light chain. b. Details of the alignment in a. The red bars indicate the mismatches between the assembled light chain sequence and the target light chain sequence.
Figure 10:
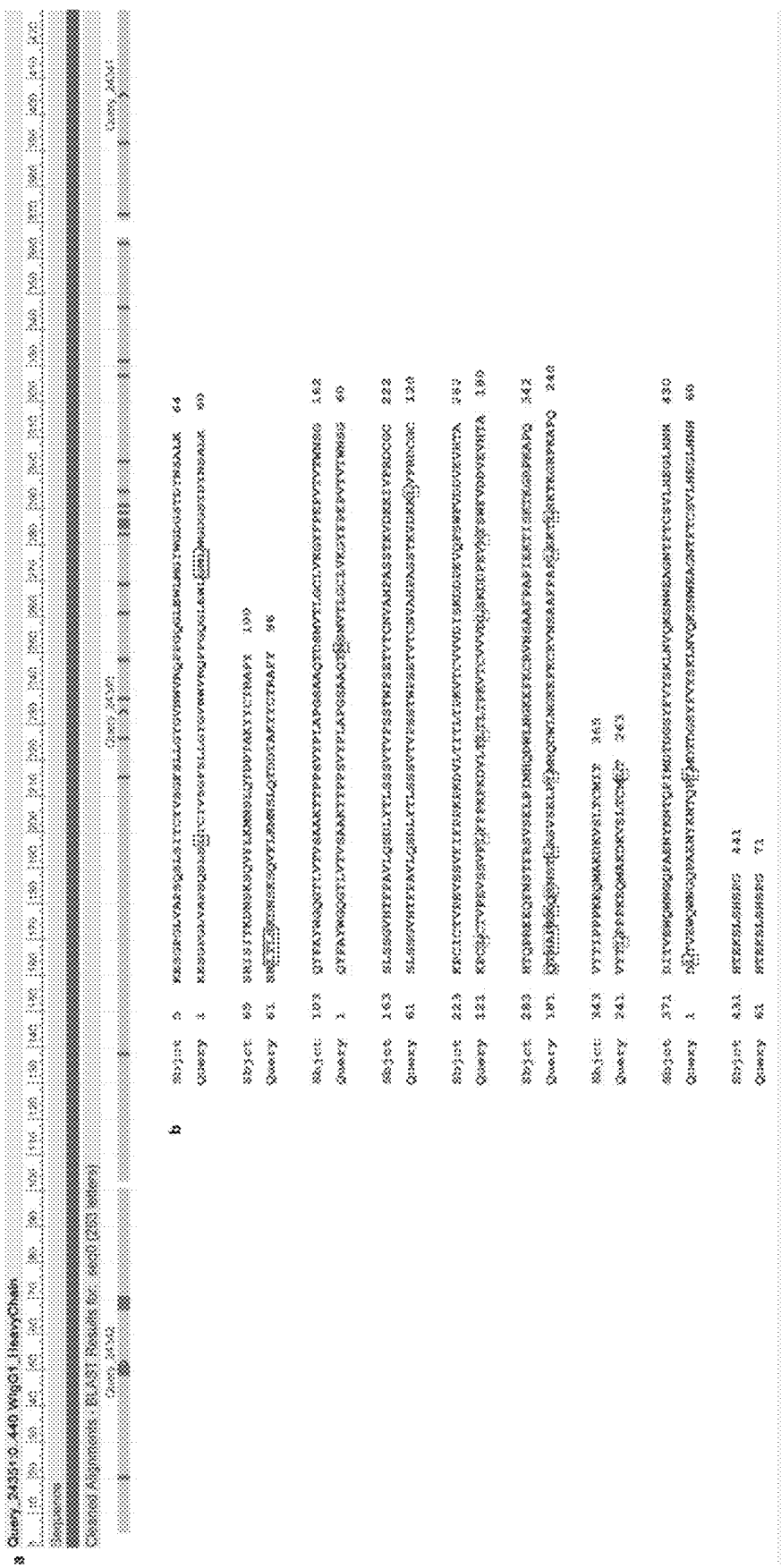
FIG. 10 shows Deepnovo assembly result for the WIgG1 heavy chain. "Sbjct" is listed as SEQ ID No:3; "Query" is listed as SEQ IS No:4. a. BLAST alignment of the top assembled contigs against the target heavy chain. b. Details of the alignment in a. The red bars indicate the mismatches between the assembled heavy chain sequence and the target heavy chain sequence.

In one embodiment, the system is applied for complete de novo sequencing of monoclonal antibodies. The DeepNovo was trained with an in-house antibody database and used it to perform de novo peptide sequencing on two antibody datasets, the WIgG1 light and heavy chains of a mouse antibody [21]. The two testing datasets were not included in the training database. De novo peptides from DeepNovo were then used by the assembler ALPS [21] to automatically reconstruct the complete sequences of the antibodies (FIGS. 9 and 10). For the light chain (length 219 amino acids), a single full-length contig was constructed that covered 100% of the target with 99.5% accuracy (218/219). For the heavy chain (length 441 amino acids), three contigs were obtained, together covering 97.5% of the target (430/441) with 97.2% accuracy (418/430). See also U.S. patent application Ser. No. 15/599,431, the entire content of which is incorporated herein by reference. This application of whole-protein sequencing previously required both de novo peptide sequencing and database search together to succeed. The present system simplifies the process to the present system alone.

Discussion

De novo peptide sequencing is a challenging and computationally intensive problem that requires both pattern recognition and global optimization on noisy and incomplete data. The present systems and methods provide a deep neural network model that uses deep learning and in some embodiments combine dynamic programming to address de novo peptide sequencing. The present systems and methods integrates CNNs and LSTM networks to learn features of tandem mass spectra, fragment ions, and sequence patterns for predicting peptides. The experiment results shown herein supports the improved performance of DeepNovo, an embodiment of the present system, over existing tools for de novo peptide sequencing.

Existing methods for de novo peptide sequencing rely heavily on rigorous global dynamic programming or graph-theoretical algorithms to address the global optimization problem. In some embodiments, the present systems and methods use knapsack, a "local" version of dynamic programming to simply filter out amino acids not suitable for the suffix mass, and do not perform backtracking. In some embodiments, (i) the neural networks in DeepNovo learn better features that can bypass the global optimization problem and (ii) DeepNovo can be further enhanced with more advanced search algorithms.

Both method and training data are factors for system performance. For example, deep learning often learn directly from raw data and require large amount of training data. Other machine learning models may rely on well-designed features based on domain-specific knowledge and may need less training data. In the embodiments described herein, DeepNovo and the training data utilized achieved better de novo sequencing results than other existing systems and methods and their respective training data. A more comprehensive benchmark study of de novo sequencing methods could be done by collecting well-annotated, gold-standard training and testing datasets.

Some database search engines and post-processors such as MS-GF+™ [50] and Percolator™ [51] allow re-training of their model parameters to adapt to a particular dataset and hence increase the peptide identification rate. Similarly, PepNovo [12] includes the option to re-train its scoring models for de novo sequencing. The present system is also re-trainable and in some embodiments provides a complete end-to-end training and prediction solution. Re-trainability is an useful feature given the massive amounts of data coming from several types of instruments, from diverse species, as well as from different experimental designs. In some embodiments, the present system is first trained on a large amount of data to obtain a general model, and then gently re-trained on a much smaller yet more targeted data source to reach the final data-specific model. Training data includes a list of spectra and their corresponding peptides, and such annotated data can be found in spectral libraries known to a skilled person, such as the NIST Mass Spectral Library or can be retrieved by using database search tools, e.g. PEAKS DB [38].

In some embodiments, the LSTM network of the present system is trained for a general model and a species-specific model. In other embodiments, the system is trained to target a particular class of instruments or fragmentation techniques.

Other applications of the system include sequence database search, which similar to de novo sequencing involves matching a spectrum to a peptide. In some applications, the system is adapted for the analysis of Data-Independent Acquisition (DIA), in particular, for inferring multiple sequences from a tandem mass spectrum that includes fragments from many different peptides. Using the LSTM recurrent neural network, the system can learn patterns of peptide sequences in addition to the fragment ion information. The additional information of sequence patterns may offer some help in addressing the ambiguity of inferring multiple peptides from a spectrum.

Computing Device

Figure 5:
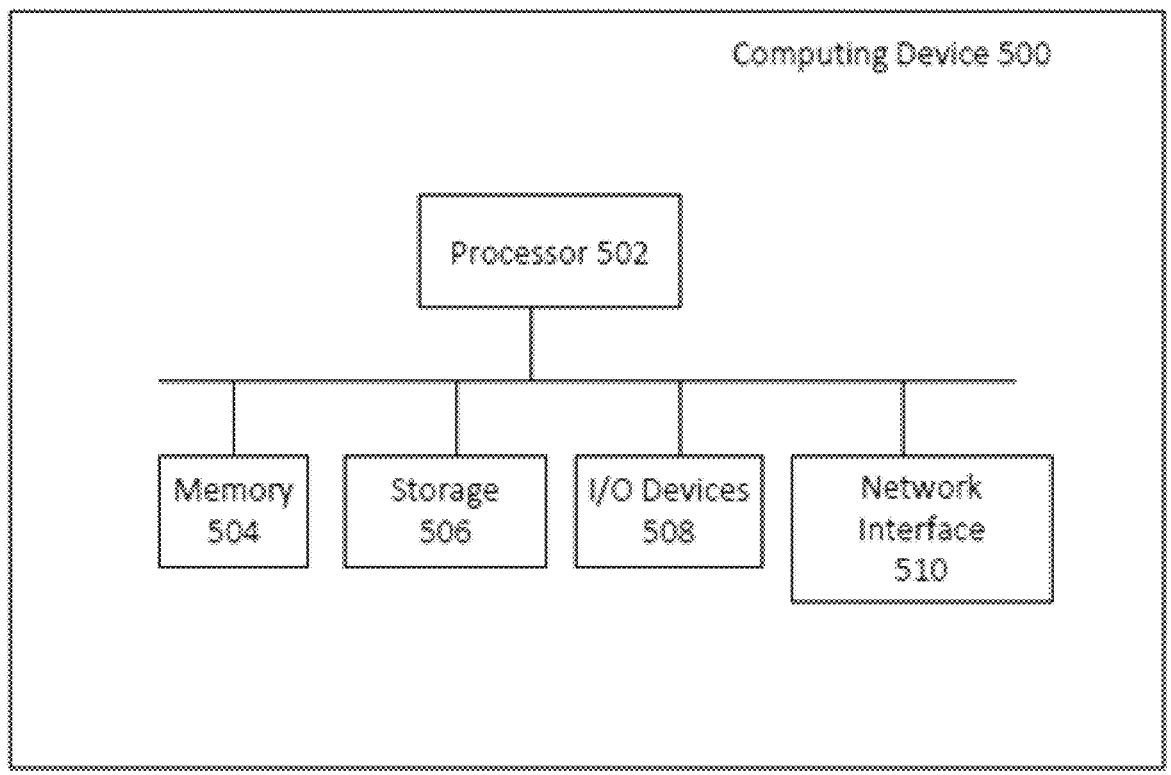
FIG. 5 is a block diagram of an example computing system configured to perform one or more of the aspects described herein.

FIG. 5 is a block diagram of an example computing device 500 configured to perform one or more of the aspects described herein. Computing device 500 may include one or more processors 502, memory 504, storage 506, I/O devices 508, and network interface 510, and combinations thereof. Computing device 500 may be a client device, a server, a supercomputer, or the like.

Processor 502 may be any suitable type of processor, such as a processor implementing an ARM or x86 instruction set. In some embodiments, processor 502 is a graphics processing unit (GPU). Memory 504 is any suitable type of random access memory accessible by processor 502. Storage 506 may be, for example, one or more modules of memory, hard drives, or other persistent computer storage devices.

I/O devices 508 include, for example, user interface devices such as a screen including capacity or other touch-sensitive screens capable of displaying rendered images as output and receiving input in the form of touches. In some embodiments, I/O devices 508 additionally or alternatively include one or more of speakers, microphones, sensors such as accelerometers and global positioning system (GPS) receivers, keypads, or the like. In some embodiments, I/O devices 508 include ports for connecting computing device 500 to other computing devices. In an example embodiment, I/O devices 508 include a universal serial bus (USB) controller for connection to peripherals or to host computing devices.

Network interface 510 is capable of connecting computing device 500 to one or more communication networks. In some embodiments, network interface 510 includes one or more or wired interfaces (e.g. wired ethernet) and wireless radios, such as WiFi, Bluetooth, or cellular (e.g. GPRS, GSM, EDGE, CDMA, LTE, or the like). Network interface 510 can also be used to establish virtual network interfaces, such as a Virtual Private Network (VPN).

Computing device 500 operates under control of software programs. Computer-readable instructions are stored in storage 506, and executed by processor 502 in memory 504. Software executing on computing device 500 may include, for example, an operating system.

The systems and methods described herein may be implemented using computing device 500, or a plurality of computing devices 500. Such a plurality may be configured as a network. In some embodiments, processing tasks may be distributed among more than one computing device 500.

While particular embodiments of the present invention have been illustrated and described, it would be obvious to those skilled in the art that various other changes and modifications can be made. The claims should therefore not be limited by the above described embodiment, systems, methods, and examples, but should be given the broadest interpretation within the scope and spirit of the invention as claimed.

REFERENCES

1. Johnson, R. S. & Biemann, K. The primary structure of thioredoxin from *Chromatium vinosum* determined by high-performance tandem mass spectrometry. Biochemistry 26, 1209-1214 (1987).
2. Martin-Visscher, L. A., van Belkum, M. J., Garneau-Tsodikova, S., Whittal, R. M., Zheng, J., McMullen, L. M., & Vederas, J. C. Isolation and characterization of carnocyclin a, a novel circular bacteriocin produced by *Carnobacterium maltaromaticum* UAL307. Appl. Environ. Microbiol. 74, 4756-4763 (2008).
3. Hatano, N. & Hamada, T. Proteome analysis of pitcher fluid of the carnivorous plant *Nepenthes alata*. J. Proteome Res. 7, 809-816 (2008).

4. Catusse, J., Strub, J. -M., Job, C., Van Dorsselaer, A. & Job, D. Proteome-wide characterization of sugarbeet seed vigor and its tissue specific expression. Proc. Natl. Acad. Sci. U.S.A. 105, 10262-10267 (2008).
5. Novo, J. V. J., Pascual, J., Lucas, R. S., Romero-Rodriguez, C., Ortega, M. R., Lenz, C. & Valledor, L. Fourteen years of plant proteomics reflected in Proteomics: moving from model species and 2DE-based approaches to orphan species and gel-free platforms. Proteomics 15, 1089-1112 (2015).
6. Taylor, J. A. & Johnson, R. S. Sequence database searches via de novo peptide sequencing by tandem mass spectrometry. Rapid Commun. Mass Spectrom. 11, 1067-1075 (1997).
7. Taylor, J. A. & Johnson, R. S. Implementation and uses of automated de novo peptide sequencing by tandem mass spectrometry. Anal. Chem. 73, 2594-2604 (2001).
8. Chen, T., Kao, M. Y., Tepel, M., Rush, J. & Church, G. M. A dynamic programming approach to de novo peptide sequencing via tandem mass spectrometry. J. Comput. Biol. 8, 325-337 (2001).
9. Dancik, D., Addona, T. A., Clauser, K. R., Vath, J. E. & Pevzner, P. A. De novo peptide sequencing via tandem mass spectrometry. J. Comp. Biol. 6, 327-342 (1999).
10. Ma, B., Zhang, K., Hendrie, C., Liang, C., Li, M., Doherty-Kirby, A. & Lajoie, G. PEAKS: powerful software for peptide de novo sequencing by tandem mass spectrometry. Rapid Commun. Mass Spectrom. 17, 2337-2342 (2003).
11. Zhang, Z. De novo peptide sequencing based on a divide-and-conquer algorithm and peptide tandem spectrum simulation. Anal. Chem. 76, 6374-6383 (2004).
12. Frank, A. & Pevzner, P. A. PepNovo: de novo peptide sequencing via probabilistic network modeling. Anal. Chem. 77, 964-973 (2005).
13. Fischer, B., Roth, V., Roos, F., Grossmann, J., Baginsky, S., Widmayer, P., Gruissem, W. & Buhmann, J. M. NovoHMM: a hidden Markov model for de novo peptide sequencing. Anal. Chem. 77, 7265-7273 (2005).
14. DiMaggio, P. A. & Floudas, C. A.: De novo peptide identification via tandem mass spectrometry and integer linear optimization. Anal. Chem. 79, 1433-1446 (2007).
15. Mo, L., Dutta, D., Wan, Y. & Chen, T. MSNovo: a dynamic programming algorithm for de novo peptide sequencing via tandem mass spectrometry. Anal. Chem. 79, 4870-4878 (2007).
16. Chi, H. et al. pNovo: de novo peptide sequencing and identification using HCD spectra. J. Proteome Res. 9, 2713-2724 (2010).
17. Jeong, K., Kim, S. & Pevzner, P. A. UniNovo: a universal tool for de novo peptide sequencing. Bioinformatics 29, 1953-1962 (2013).
18. Chi, H. et al. pNovo+: de novo peptide sequencing using complementary HCD and ETD tandem mass spectra. J. Proteome Res. 12, 615-625 (2013).
19. Ma, B. Novor: real-time peptide de novo sequencing software. J. Amer. Soc. Mass Spectrom. 26, 1885-1894 (2015).
20. Maggon, K. Monoclonal antibody "gold rush". Curr. Med. Chem. 14, 1978-1987 (2007).
21. Tran., N. H., Rahman, M. Z., He, L., Xin, L., Shan, B. Z. & Li, M. Complete de novo assembly of monoclonal antibody sequences. Scientific Reports 6, 31730 (2016).
22. Bandeira, N., Pham, V., Pevzner, P., Arnott, D. & Lill, J. R. Automated de novo protein sequencing of monoclonal antibodies. Nat. Biotechnol. 26, 1336-1338 (2008).
23. Guthals, A., Clauser, K. R., Frank, A. M., & Bandeira, N. Sequencing-grade de novo analysis of MS/MS triplets (CID/HCD/ETD) from overlapping peptides. J. Proteome Res. 12, 2846-2857 (2013).
24. Ma, B. & Johnson, R. De novo sequencing and homology searching. Mol. Cell Proteomics 11, O111.014902. (2012).
25. LeCun, Y., Bengio, Y. & Hinton, G. Deep learning. Nature 521, 436-444 (2015).
26. Ciresan, D., Giusti, A., Gambardella, L. M. & Schmidhuber, J. Deep neural networks segment neuronal membranes in electron microscopy images. In Proc. Advances in Neural Information Processing Systems 25, (2012).
27. Krizhevsky, A., Sutskever, I. & Hinton, G. ImageNet classification with deep convolutional neural networks. In Proc. Advances in Neural Information Processing Systems 25, (2012).
28. Hinton, G. et al. Deep neural networks for acoustic modeling in speech recognition: the shared views of four research groups. IEEE Signal Processing Magazine. 29, 82-97 (2012).
29. Sutskever, I., Vinyals, O. & Le, Q. Sequence to sequence learning with neural networks. In Proc. Advances in Neural Information Processing Systems 27, 3104-3112 (2014).
30. Rusk, N. Deep learning. Nat. Methods 13, 35 (2016).
31. Zhou, J. & Troyanskaya, O. G. Predicting effects of noncoding variants with deep learning based sequence model. Nat. Methods 12, 931-934 (2015).
32. Alipanahi, B., Delong, A., Weirauch, M. T. & Frey, B. J. Predicting the sequence specificities of DNA- and RNA-binding proteins by deep learning. Nat. Biotechnology 33, 831-838 (2015).
33. Wang, S., Sun, S., Li, Z., Zhang, R. & Xu, J B. Accurate de novo prediction of protein contact map by ultra-deep learning model. PLoS Comput. Biol. 13, e1005324 (2017).
34. Hochreiter, S. & Schmidhuber, J. Long short-term memory. Neural Computation 9, 1735-1780 (1997).
35. Karpathy, A. & Li, F. F. Deep visual-semantic alignments for generating image description. IEEE Conference on Computer Vision and Pattern Recognition (CVPR), 3128-3137 (2015).
36. Vinyals, O., Toshev, A., Bengio, S. & Erhan, D. Show and tell: a neural image caption generator. IEEE Conference on Computer Vision and Pattern Recognition (CVPR), 3156-3164 (2015).
37. Mikolov, T., Sutskever, I., Chen, K., Corrado, G. & Dean, J. Distributed representations of words and phrases and their compositionality. In Proc. Advances in Neural Information Processing Systems 26, 3111-3119 (2013).
38. PEAKS Studio (version 8.0). Bioinformatics Solutions Inc, Waterloo, Ontario, Canada (http://www.bioinfor.com/).
39. Grosche A. et al. The proteome of native adult Muller Glial cells from murine retina. Mol. Cell. Proteomics 15, 462-480 (2016).
40. Marza, E. et al. Genome-wide screen identifies a novel p97/CDC-48-dependent pathway regulating ER-stress-induced gene transcription. EMBO Rep. 16, 332-340 (2015).
41. Pettersen, V. K., Mosevoll, K. A., Lindemann, P. C. & Wiker, H. G. Coordination of metabolism and virulence factors expression of extraintestinal pathogenic *Escherichia coli* purified from blood cultures of patients with sepsis. Mol. Cell. Proteomics 15, 2890-2907 (2016).

42. Hampoelz B. et al. Pre-assembled nuclear pores insert into the nuclear envelope during early development. Cell 166, 664-678 (2016).
43. Zhang, Y. et al. Tissue-based proteogenomics reveals that human testis endows plentiful missing proteins. J. Proteome. Res. 14, 3583-3594 (2015).
44. Hebert A. S. et al. The one hour yeast proteome. Mol Cell. Proteomics. 13, 339-347 (2014).
45. Peng, J., Cao, J., Ng, F. M. & Hill, J. *Pseudomonas aeruginosa* develops Ciprofloxacin resistance from low to high level with distinctive proteome changes. J. Proteomics. 152, 75-87 (2017).
46. Inglese, P. et al. Deep learning and 3D-DESI imaging reveal the hidden metabolic heterogeneity of cancer. Chem. Sci., (2017).
47. Davis, J. & Goadrich, M. The relationship between Precision-Recall and ROC curves. Proceedings of the 23rd International Conference on Machine Learning, 233-240 (2006).
48. Steen, H. & Mann, M. The abc's (and xyz's) of peptide sequencing. Nat. Rev. Mol. Cell Biol., 699-711 (2004).
49. Kingma, D. P. & Ba, J. Adam: a method for stochastic optimization. arXiv:1412.6980.
50. Kim, S. & Pevzner, P. A. MS-GF+ makes progress towards a universal database search tool for proteomics. Nat. Commun. 5, 5277 (2014).
51. Kall, L., Cantebury, J. D., Weston, J., Noble, W. S. & MacCoss, M. J. Semi-supervised learning for peptide identification from shotgun proteomics datasets. Nat. Methods 4, 923-925 (2007).
52. Paiva, A. L., Oliveira, J. T., de Souza, G. A. & Vasconcelos, I. M. Label-free proteomics reveals that Cowpea severe mosaic virus transiently suppresses the host leaf protein accumulation during the compatible interaction with Cowpea (*Vigna unguiculata* [L.] Walp.). J. Proteome Res., 15, 4208-4220 (2016).
53. Nevo, N. et al. Impact of cystinosin glycosylation on protein stability by differential dynamic stable isotope labeling by amino acids in cell culture (SILAC). Mol. Cell Proteomics, 16, 457-468 (2017).
54. Cassidy, L., Prasse, D., Linke, D., Schmitz, R. A. & Tholey, A. Combination of bottom-up 2DLC-MS and semi-top-down GelFree-LC-MS enhances coverage of proteome and low molecular weight short open reading frame encoded peptides of the Archaeon *Methanosarcina mazei*. J. Proteome Res., 15, 3773-3783 (2016).
55. Reuß, D. R. et al. Large-scale reduction of the *Bacillus subtilis* genome: consequences for the transcriptional network, resource allocation, and metabolism. Genome Res., 27, 289-299 (2017).
56. Petersen, J. M. et al. Chemosynthetic symbionts of marine invertebrate animals are capable of nitrogen fixation. Nat. Microbiol., 2, 16195 (2016).
57. Mata, C. I. et al. In-depth characterization of the tomato fruit pericarp proteome. Proteomics, 17, 1-2 (2017).
58. Seidel, G. et al. Quantitative global proteomics of Yeast PBP1 deletion mutants and their stress responses identifies glucose metabolism, mitochondrial, and stress granule changes. J. Proteome Res., 16, 504-515 (2017).
59. Hu, H. et al. Proteome analysis of the hemolymph, mushroom body, and antenna provides novel insight into honeybee resistance against *varroa* infestation. J. Proteome Res., 15, 841-854 (2016).
60. Cypryk, W. et al. Proteomic and bioinformatic characterization of extracellular vesicles released from human macrophages upon Influenza A virus infection. J. Proteome Res., 16, 217-227 (2017).
61. LeCun, Y. et al. Backpropagation applied to handwritten zip code recognition. Neural Comput. 11, 541-551 (1989).
62. Glorot, X., Bordes, A. & Bengio, Y. Deep sparse rectifier neural networks. Proceedings of the Fourteenth International Conference on Artificial Intelligence and Statistics (AISTATS), (2011).
63. Srivastava, N., Hinton, G., Krizhevsky, A., Sutskever, I. & Salakhutdinov, R. Dropout: a simple way to prevent neural networks from overfitting. J. Mach. Learn. Res. 15, 1929-1958 (2014).

The invention claimed is:

1. A computer implemented system for de novo sequencing of peptides from mass spectrometry data using neural networks, the computer implemented system comprising:
a processor and at least one memory providing a plurality of layered nodes configured to form an artificial neural network for generating a probability measure for one or more candidates to a next amino acid in an amino acid sequence, the artificial neural network trained on known mass spectrometry spectrum data containing a plurality of known fragment ions peaks of known sequences differing in length and differing by one or more amino acids;
wherein the plurality of layered nodes receives a mass spectrometry spectrum data as input, the plurality of layered nodes comprising:
at least one convolutional layer for filtering mass spectrometry spectrum data to detect fragment ion peaks corresponding to amino acid sequences of various lengths; and
at least one fully-connected layer for identifying pairs of:
a) a fragment ion peak corresponding to a sequence that is one amino acid longer than the determined amino acid sequence, and
b) a fragment ion peak corresponding to a sequence that is one amino acid less than the remaining undetermined amino acid sequence of the peptide,
by fitting the plurality of known fragment ion peaks against the mass spectrometry spectrum data, and for outputting the probability measure for each candidate next amino acid;
the processor configured to:
obtain an input prefix representing a determined amino acid sequence of the peptide,
identify a next amino acid based on a candidate next amino acid having a greatest probability measure based on the output of the artificial neural network and the mass spectrometry spectrum data of the peptide; and
update the determined amino acid sequence with the next amino acid.

2. The system of claim 1, comprising a mass spectrometer configured to generate a mass spectrometry spectrum data of a peptide.

3. The system of claim 1, wherein the plurality of layered nodes receives an image data or a vector data representing the mass spectrometry spectrum data as input, and output a probability measure vector.

4. The system of claim 1, wherein the processor is configured to determine the entire sequence of the peptide by obtaining the probability measures of candidates at a number of points in the sequence and beam searching.

5. The system of claim 1, wherein the plurality of layered nodes comprise a first convolutional layer for applying one or more filters to the mass spectrometry spectrum data using a 4-dimensional kernel and a bias term.

6. The system of claim 5, wherein the plurality of layered nodes comprise a second convolutional layer for applying further one or more filters using an additional 4-dimensional kernel.

7. The system of claim 5, wherein a first dropout is applied after the first convolutional layer.

8. The system of claim 6, wherein a second dropout is applied after the second convolutional layer.

9. The system of claim 1, wherein the plurality of layered nodes comprise a first fully-connected layer having as many neuron units as there are outputs from the at least one convolutional layer, and a second fully-connected layer comprising as many neuron units as there are possible entries for the next amino acid.

10. The system of claim 1, wherein the system is configured to bi-directionally sequence the peptide using two separate sets of parameters, wherein one set comprises parameters for forward sequencing and the other set comprises parameters for backward sequencing.

11. The system of claim 1, wherein a pair of fragment ion peaks are filtered out when the sum of:
a mass corresponding to the fragment ion peak of a), and
a mass corresponding to the fragment ion peak of b)
exceed the total mass of the peptide.

12. The system of claim 1, wherein the artificial neural network is further trained on a database of known peptide sequences; and
wherein the plurality of layered nodes comprise:
one or more layers comprising a convolutional neural network (CNN) for identifying the presence of amino acids in the mass spectrometry spectrum data and generate one or more output vectors representing a list of amino acids present in the peptide; and one or more layers comprising a recurrent neural network (RNN) for predicting the next amino acid by vector embedding the one or more output vectors, and for outputting the probability measure for each candidate next amino acid.

13. The system of claim 12, wherein the one or more layers of the plurality of layered nodes comprising the RNN is a long short-term memory network (LSTM).

14. They system of claim 13, wherein the one or more layers of the plurality of layered nodes comprising the LSTM comprises 2 or 3 layers.

15. The system of claim 14, wherein the one or more layers of the plurality of layered nodes comprising the LSTM comprise a last fully-connected layer having as many neuron units as there are possible entries for the next amino acid.

16. The system of claim 13, wherein the one or more layers of the LSTM is for predicting the next amino acid by embedding the output vector to form a two-dimensional array by iterating according to the following equation, $x_0 = CNN_{spectrum}(I)$ $x_{t-1} = Embedding_{a_{t-1},*}, t>1$ $s_t = LSTM(x_{t-1})$ where I is the spectrum intensity vector, $a_{(t-1)}$ is the symbol predicted at iteration t-1, $Embedding_{(i,*)}$ is the row i of the embedding array, and $s_t$ is the output of the LSTM and will be used to predict the symbol at iteration t.

17. The system of claim 12, wherein the one or more layers comprising the CNN is for identifying the presence of amino acids in the mass spectrometry spectrum data by fitting known single or multiple amino acid long fragment ion peaks to the mass spectrometry spectrum data.

18. The system of claim 12, wherein the one or more layers comprising the CNN is for identifying the presence of amino acids in the mass spectrometry spectrum data by identifying two fragment ion peaks that differ by one amino acid.

19. The system of claim 1, wherein the processor is configured to convert the mass spectrometry spectrum data into an intensity vector listing an intensity value for each mass range over the mass spectrometry spectrum data.

20. The system of claim 19, wherein the processor is configured to:
slice the intensity vector by subdividing the mass ranges, such that the sliced intensity vector lists intensity values for mass ranges corresponding to multiples of the mass of an amino acid, and
generate an input array comprising a plurality of sliced intensity vectors each corresponding to a different amino acid.

21. A computer implemented system for de novo sequencing of peptides from mass spectrometry data using neural networks, the computer implemented system comprising:
a processor and at least one memory providing a plurality of layered nodes configured to form an artificial neural network for generating a probability measure for one or more candidates to a next amino acid in an amino acid sequence, the artificial neural network trained on:
known mass spectrometry spectrum data containing a plurality of known fragment ions of known sequences differing in length and differing by one or more amino acids, and
a database of known peptide sequences;
wherein the plurality of layered nodes receives a mass spectrometry spectrum data as input, the plurality of layered nodes comprising a first set of layered nodes and a second set of layered nodes;
wherein the first set of layered nodes comprises:
at least one convolutional layer for filtering mass spectrometry spectrum data to detect fragment ion peaks; and
at least one fully-connected layer for identifying pairs of:
a) a fragment ion peak corresponding to a sequence that is one amino acid longer than the determined amino acid sequence, and
b) a fragment ion peak corresponding to a sequence that is one amino acid less than the remaining undetermined amino acid sequence of the peptide,
by fitting the plurality of known fragment ions peaks against the mass spectrometry spectrum data;
wherein the second set of layered nodes comprises:
one or more layers comprising a convolutional neural network (CNN) for identifying the presence of amino acids in the mass spectrometry spectrum data and generate one or more output vectors representing a list of amino acids present in the peptide; and
one or more layers comprising a recurrent neural network (RNN) for predicting the next amino acid by vector embedding the one or more output vectors;
wherein the first and second set of layered nodes share at least one common last fully-connected layer for outputting the probability measure for each candidate next amino acid;
the processor configured to:
obtain an input prefix representing a determined amino acid sequence of the peptide,
identify a next amino acid based on a candidate next amino acid having a greatest probability measure based on the output of the artificial neural network and the mass spectrometry spectrum data of the peptide; and
update the determined amino acid sequence with the next amino acid.

22. The system of claim 21, wherein the first and second neural networks share a first and a second common last fully-connected layer, wherein the first common last fully-connected layer is for concatenating the outputs from the first and second neural networks, and the second fully-connected layer comprises as many neuron units as there are possible candidates the next amino acid.

23. A method for de novo sequencing of peptides from mass spectrometry data using neural networks, the method comprising:
obtaining a mass spectrometry spectrum data of a peptide;
filtering the mass spectrometry spectrum data to detect fragment ion peaks corresponding to amino acid sequences of various lengths by at least one convolutional layer of a plurality of layered nodes configured to form an artificial neural network for generating a probability measure for one or more candidates to a next amino acid in an amino acid sequence, wherein the artificial neural network is trained on known mass spectrometry spectrum data containing a plurality of known fragment ions peaks of known sequences differing in length and differing by one or more amino acids;
fitting the plurality of known fragment ions peaks of known sequences against the mass spectrometry spectrum data to identifying pairs of:

a) a fragment ion peak corresponding to a sequence that is one amino acid longer than the determined amino acid sequence, and b) a fragment ion peak corresponding to a sequence that is one amino acid less than the remaining undetermined amino acid sequence of the peptide, by at least one fully-connected layer of the plurality of layered nodes;

outputting a probability measure for each candidate of a next amino acid;

obtaining an input prefix representing a determined amino acid sequence of the peptide;

identifying a next amino acid based on a candidate next amino acid having a greatest probability measure based on the output of the artificial neural network and the mass spectrometry spectrum data of the peptide; and updating the determined amino acid sequence with the next amino acid.

24. The method of claim 23, wherein the known fragment ion peaks of known sequences differ in length and differ by one or more amino acids, and wherein the method comprises training the artificial neural network on the known fragment ion peaks.

25. The method of claim 24, comprising filtering out a pair of fragment ion peaks when the sum of:

a mass corresponding to the fragment ion peak of a), and a mass corresponding to the fragment ion peak of b)

exceed the total mass of the peptide.

26. The method of claim 23, comprising:

identifying the presence of amino acids in the mass spectrometry spectrum data by one or more layers of the plurality of layered nodes comprising a convolutional neural network;

generating one or more output vectors representing a list of amino acids present in the peptide;

predicting a next amino acid by vector embedding the one or more output vectors by one or more layers of the plurality of layered nodes comprising a recurrent neural network.

27. The method of claim 26, comprising training the plurality of layered nodes on:

known mass spectrometry spectrum data containing a plurality of known fragment ions of known sequences differing in length and differing by one or more amino acids, and a database of known peptide sequences.

28. The method of claim 26, comprising identifying the presence of amino acids in the mass spectrometry spectrum data by fitting known single or multiple amino acid long fragment ion peaks to the mass spectrometry spectrum data.

29. The method of claim 26, comprising identifying the presence of amino acids in the mass spectrometry spectrum data by identifying two fragment ion peaks that differ by one amino acid.

30. The method of claim 23, comprising converting the mass spectrometry spectrum data into an intensity vector listing an intensity value for each mass range over the mass spectrometry spectrum data.

31. The method of claim 30, comprising converting the mass spectrometry spectrum data into an intensity vector listing intensity values for mass ranges over the mass spectrometry spectrum data, and the plurality of layered nodes receives the intensity vector as input and output a probability measure vector.

32. The method of claim 31, comprising slicing the intensity vector by subdividing the mass ranges, such that the sliced intensity vector lists intensity values for mass ranges corresponding to multiples of the mass of an amino acid, and generating an input array comprising a plurality of sliced intensity vectors each corresponding to a different amino acid.

* * * * *